US006989443B2

(12) United States Patent
Wu et al.

(10) Patent No.: US 6,989,443 B2
(45) Date of Patent: Jan. 24, 2006

(54) CARBORANYLPORPHYRINS AND USES THEREOF

(75) Inventors: Haitao Wu, Wading River, NY (US); Michiko Miura, Hampton Bays, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 152 days.

(21) Appl. No.: 10/878,138

(22) Filed: Jun. 28, 2004

(65) Prior Publication Data

US 2005/0287073 A1    Dec. 29, 2005

(51) Int. Cl.
*C07B 47/00* (2006.01)
*A61B 5/055* (2006.01)
*C07F 5/10* (2006.01)
*A61K 31/555* (2006.01)

(52) U.S. Cl. .................. 540/145; 424/9.362; 424/9.61; 514/185; 514/410; 534/15

(58) Field of Classification Search ............. 424/9.362, 424/9.61; 540/145; 534/15; 514/185, 410
See application file for complete search history.

(56) References Cited

U.S. PATENT DOCUMENTS

| | | | |
|---|---|---|---|
| 4,783,529 A | 11/1988 | Lavallee et al. | |
| 4,959,356 A | 9/1990 | Miura et al. | |
| 5,149,801 A | 9/1992 | Kahl et al. | |
| 5,162,231 A | 11/1992 | Cole et al. | |
| 5,268,371 A | 12/1993 | Mauclaire et al. | |
| 5,312,896 A | 5/1994 | Bhardwaj et al. | |
| 5,563,132 A | 10/1996 | Bodaness | |
| 5,654,423 A | 8/1997 | Kahl et al. | |
| 5,674,467 A | 10/1997 | Maier et al. | |
| 5,877,165 A | 3/1999 | Miura et al. | |
| 5,955,586 A | 9/1999 | Sessler et al. | |
| 6,010,805 A | 1/2000 | Scanlon, Jr. et al. | |
| 6,066,628 A | 5/2000 | Stojiljkovic et al. | |
| 6,566,517 B2 | 5/2003 | Miura et al. | |
| 2003/0032799 A1 | 2/2003 | Miura et al. | |
| 2003/0083494 A1 | 5/2003 | Miura et al. | |

FOREIGN PATENT DOCUMENTS

WO    WO 01/85736 A1    11/2001

OTHER PUBLICATIONS

Harth et al. The Effect of Macromolecular Architecture in Nanomaterials: A comparison of Site Isolation in Polyphyrin Core Dedrimers and Their Isomeric Linear Analogues. J. Am. Chem Soc. 2002, 124, pp. 3926-3938.*
Morris et al., "Porphyrin-mediated boron-neutron capture therapy: evaluation of the reactions of skin and central nervous system," *Int. J. Radiat. Biol.*, 79(3): 149-158 (2003).
Vincente, et al., "Synthesis, dark toxicity and induction of in vitro DNA photodamage by a tetra (4-nido-carboranylphenyl)prophyrin," *J. Photochem. Photobiol. B, Biology*, 68(2-3): 123-132 (2002).
Maderna et al., "Synthesis of a porphyrin-labelled carboranyl phosphate diester: a potential new drug for boron neutron capture therapy of cancer," *Chem. Commun.*, 16: 1784-1785 (2002).
Miura et al., "Boron Neutron Capture of a Marine Mammary Carcinoma using a Lipophilic Carboranyltetraphenylporphyrin," *Radiat. Res.*, 155(4): 603-610 (2001).
Miura et al., "Evaluation of carborane-containing porphyrins as tumor targeting agents for boron neutron capture therapy," *Br. J. Radiol.*, 71(847): 773-781 (1998).
Miura et al., "Synthesis of a Nickel Tetracarboranyltetraphenylporphyrin for Boron Neutro-Capture Therapy: Biodistribution and Toxicity in Tumor-Bearing Mice," *Int. J. Cancer.*, 68(1): 114-119 (1996).
Kahl et al., "A Carboranyl Porphyrin for Boron Neutron Capture Therapy of Brain Tumors," *Basic Life Sci.*, 50: 193-203 (1989).
Miura et al., "Biodistribution of copper carboranyltetraphenylporphyrins in rodents bearing an isogeneic or human neoplasm," *J. NeuroOncol*, 5,: 111-117 (2001).
Berlin et al., "Are Porphyrin Mixtures Favorable Photodynamic Anticancer Drugs? A Model Study with Combinatorial Libraries of Tetraphenylporphyrins," *Combinatorial Chemistry*, 61(2): 107-118 (1998).
Miller et al., "In Vivo Animal Studies with Gadolinium (III) Texaphyrin As a Radiation Enhancer," *Int. J. Radiat. Oncol. Biol. Phys.*, 45(4): 981-989 (1999).
Bhyrappa et al., "Octabromotetraphenylporphyrin and Its Metal Derivatives: Electronic Structure and Electrochemical Properties," *Inorg. Chem.*, 30: 239-245 (1991).
Birnbaum et al., $^{n19}$F NMR Spectra and Structures of Halogenated Porphyrins,*Inorg. Chem.*, 34(14): 3625-3632 (1995).

(Continued)

Primary Examiner—Richard Raymond
Assistant Examiner—Matthew L. Fedowitz
(74) Attorney, Agent, or Firm—Margaret C. Bogosian

(57) ABSTRACT

The present invention is directed to low toxicity boronated compounds and methods for their use in the treatment, visualization, and diagnosis of tumors. More specifically, the present invention is directed to low toxicity carborane-containing 5, 10, 15, 20-tetraphenylporphyrin compounds and methods for their use particularly in boron neutron capture therapy (BNCT) and photodynamic therapy (PDT) for the treatment of tumors of the brain, head, neck, and surrounding tissue. The invention is also directed to using these carborane-containing tetraphenyl porphyrin compounds to methods of tumor imaging and/or diagnosis such as MRI, SPECT, or PET.

56 Claims, No Drawings

OTHER PUBLICATIONS

Fairchild et al., "Current Status of [10]B-Neutron Capture Therapy: Enhancement of Tumor Dose Via Beam Filtration and Dose Rate, and the Effects of These Parameters on Minimum Boron Content: a Theoretical Evaluation," *Int. J. Radiat. Oncol. Biol. Phys.,* 11(4): 831-840 (1985).

Woller et al., "2, 3, 7, 8, 12, 13, 17, 18-Octafluoro-5, 10, 15, 20-tetraarylporphyrins and Their Zinc Complexes: First Spectroscopic, Electrochemical, and Structural Characterization of a Perfluorinated Tetraarylmetalloporphyrin," *J. Org. Chem.,* 62(6): 1588-1593 (1997).

Woller et al., "A Straightforward Synthesis of 3,4-Difluoropyrrole," *J. Org. Chem.,* 63(6): 5706-5707 (1998).

Ozette et al., "New Metalloporphyrins with Extremely Altered Redox Properties: Synthesis, Structure, and Facile Reduction to Air-Stable n-Anion Radicals of Zinc and Nickel β-Heptanitroporphyrins," *J. Am. Chem. Soc.,* 119 (27): 6442-6443 (1997).

Chanana et al., "Boron Neutron Capture Therapy for Glioblastoma Multiforme: Interim Results from the Phase I/II Dose-Escalation Studies," *Neurosurgery,* 44(6): 1182-1193 (1999).

Vincente et al., "Synthesis of carbon—carbon linked carboranylated porphyrins for boron neutron capture therapy of cancer." *Tetrahedron Letters,* 41: 7623-7627 (2000).

Evstigneeva, "Synthesis of Carboranylporphyrins and the Perspectives of Their Use for Boron Neutron Capture Therapy," *Molecules,* 5: 1479-80.

Zakharkin et al., "Synthesis of carboranyl derivatives of deuteroporphyrin 1X," *Russian Chemical Bulletin,* 48(12): 2312-14 (1999).

"Brain Tumor Patients offered New Hope with Expanded Trial of Promising Therapy," Press Release, Brookhaven National Labs, Nov. 1998, <http://virtualtrials.com/bnct2.cfm,>.

Yarris, "Accelerator for Boron Neutron Capture Therapy Proposed by Lab," Jun. 21, 1996, Lawrence Berkeley National Laboratory, <http://www.lbl.gov/Science-Articles/Archive/boron-capture.html>.

Gomez, "Boron Neutron Capture Therapy (BNCT)," Dec. 1, 1998, Lawrence Berkeley National Laboratory, <http://www.virtualtrials.com/bnct.cfm>.

Chu et al., Overview—LBNL/UCSF Boron Neutron Capture Proposal, <http://ehs.lbl.gov/bnct/overview.html>.

Chu et al., Work In Progress—LBNL/UCSF Boron Neutron Capture Proposal, "Progress Report (Apr. 1997) on 'Accelerator-Based BNCT Clinical Trial'," <http://ehs.lbl.gov/bnct/progress.html>.

Ludewigt et al., "Research Topics and Papers, Neutron Production target for the BNCT Project at Lawrence Berkeley National Laboratory and at the University of California at San Francisco, Project 2b—Neutron Production Target," <http://ehs.lbl.gov/bnct/research/target.html>.

Larson et al., "Research Topics and Papers, Phase I Study Concept for the BNCT Project at Lawrence Berkeley National Laboratory and at the University of California at San Francisco, Project 11—Proposed BNCT Clinical Trials," <http://ehs.lbl.gov/bnct/research/proposedtrials.html>.

Deen et al, "Research Topics and Papers, Small Animal and In Vitro Toxicity and Biodistribution for the BNCT Project at Lawrence Berkeley National Laboratory and at the University of California at San Francisco, Project 6- Small Animal and In Vitro Toxicity, Biodistribution and Radiobiology," http://ehs.lbl.gov/bnct/research/smallanimal.html>.

Fike et al, "Research Topics and Papers, Small Animal and In Vitro Toxicity and Biodistribution for the BNCT Project at Lawrence Berkeley National Laboratory and at the University of California at San Francisco, Project 7-Large Animal Pharmacology and Toxicology," http://ehs.lbl.gov/bnct/research/largeanimal.html>.

* cited by examiner

CARBORANYLPORPHYRINS AND USES THEREOF

This invention was made with Government support under contract number DE-AC02-98CH10886, awarded by the U.S. Department of Energy. The Government has certain rights in the invention.

BACKGROUND OF THE INVENTION

The efficacy of radiation and chemical methods in the treatment of cancers has been limited by a lack of selective targeting of tumor cells by the therapeutic agent. In an effort to spare normal tissue, current tumor treatment methods have therefore restricted radiation and/or chemical treatment doses to levels that are well below optimal or clinically adequate. Thus, designing compounds that are capable, either alone or as part of a therapeutic method, of selectively targeting and destroying tumor cells, is a field of intense study.

Because of the known affinity of porphyrins to neoplastic tissues, there has been intense interest in using porphyrins as delivery agents in the treatment of neoplasms in the brain, head and neck, and related tumors. Porphyrins in general belong to a class of colored, aromatic tetrapyrrole compounds, some of which are found naturally in plants and animals, e.g., chlorophyll and heme, respectively.

Porphyrins and other tetrapyrroles with relatively long singlet lifetimes have already been used to treat malignant tumors using photodynamic therapy (PDT). In PDT, the patient is first injected with a photosensitizing drug, typically a porphyrin. The tumor cells, now photosensitized, are susceptible to destruction when exposed to an intense beam of laser red light. The biochemical mechanism of cell damage in PDT is believed to be mediated largely by singlet oxygen, which is produced by transfer of energy from the light-excited porphyrin molecule to an oxygen molecule. However, PDT has been limited predominantly by the photosensitizing compounds, which have lower than adequate selectivity to tumor cells and higher than optimal toxicity to normal tissue.

A promising new form of cancer therapy is boron neutron-capture therapy (BNCT). BNCT is a bimodal cancer treatment based on the selective accumulation of a stable nuclide of boron known as boron-10, or $^{10}B$, in the tumor, followed by irradiation of the tumor with thermalized neutrons. The thermalized neutrons impinge on the boron-10, causing a nuclear fission (decay reaction). The nuclear fission reaction causes the highly localized release of vast amounts of energy in the form of high linear-energy-transfer (LET) radiation, which can kill cells more efficiently (higher relative biological effect) than low LET radiation, such as x-rays.

In BNCT, the boron-containing compound must be non-toxic or of low toxicity when administered in therapeutically effective amounts, as well as being capable of selectively accumulating in cancerous tissue. For example, clinical BNCT for malignant brain tumors was carried out at the Brookhaven National Laboratory Medical Department using p-boronophenylalanine (BPA) as the boron carrier (Chanana et al., *Neuro surgery*, 44, 1182–1192, 1999). Although BPA has the advantage of low chemical toxicity, it accumulates in critical normal tissues at levels that are less than desirable. In particular, the tumor-to-normal brain and tumor-to-blood boron concentrations are in the ratio of approximately 3:1. Such low specificity limits the maximum dose of BPA to a tumor since the allowable dose to normal tissue will be the limiting factor.

A particular class of synthetic porphyrins, known as tetraphenyl porphyrins, have garnered intense interest in the design of new boron carrier compounds for BNCT. Tetraphenylporphyrins (TPPs) contain four phenyl groups, typically on the 5, 10, 15, and 20 positions of the porphyrin ring. An advantage of TPPs is their ease of synthesis.

The solubility of TPPs can be controlled by the substituents, generally on the phenyl positions. Those TPPs containing sulfonates or carboxylates are water-soluble. However, some of the carborane-containing TPPs have high lipophilic properties, which can require high amounts of non-aqueous excipients before administration into animals. High amounts of excipients may reduce the biological effect of the porphyrin by, for example, changing the microlocalization within the tumor cell such that it may be bound to membranes instead of being homogeneously distributed throughout the cell. In addition, the use of more hydrophilic bonds such as amide, ester, or urea bonds, although significantly more hydrophilic than carbon-carbon linkages, are known to hydrolyze under numerous types of conditions. Such hydrolysis is particularly problematic when such hydrophilic bonds are employed to attach the carboranyl group to the porphyrin molecule, since hydrolysis results in loss of the carbonyl group before reaching the target.

Therefore, there continues to be an effort to reduce the lipophilic behavior of TPPs while not compromising their chemical stability. For example, international Patent Application No. WO 01/85736 by Vicente et al describes the synthesis and use of tetraphenylporphyrin compounds that contain hydrophilic groups. A salient feature of the Vicente compounds is the attachment of the carboranyl group to the phenyl group by, exclusively, a carbon-carbon linkage. Although such a carbon-carbon linkage is not prone to hydrolysis or other chemical attack, such a linkage is significantly hydrophobic.

Porphyrins also have the advantage of having the ability to chelate metal ions in its interior. Such chelated porphyrins can additionally function as visualization tools for real-time monitoring of porphyrin concentration and/or diagnostic agents. For example, when chelated to paramagnetic metal ions, porphyrins may function as contrast agents in magnetic resonance imaging (MRI), and when chelated to radioactive metal ions, porphyrins may function as imaging agents for single photon emission computed tomography (SPECT) or positron emission tomography (PET).

In addition, by using chelated boron-containing porphyrins in BNCT, boron concentration and distribution in and around the tumor and all tissues within the irradiated treatment volume can be accurately and rapidly determined noninvasively before and during the irradiation. Such diagnostic information allows BNCT treatment to be performed more quickly, accurately, and safely, by lowering exposures of epithermal neutrons in regions of tissues known to contain high levels of boron. Short irradiations would obviate the inconvenience and discomfort to the patient of long and often awkward positioning of the head at a reactor port. However, the anticipated use of acceleratorgenerated neutrons would likely produce a significantly lower flux and hence effect longer irradiation times, so that compounds that have longer tumor retention times would become critical.

Accordingly, there is a need for new compounds, especially boron-containing porphyrins, with long retention times in tumors, and that selectively target and destroy tumor cells with minimal damage to normal tissue. In addition, there is a need for more effective methods for the treatment of brain, head and neck, and related tumors, and more particularly, more effective BNCT treatments and boron-delivery compounds used therein.

SUMMARY OF THE INVENTION

The present invention is directed to low toxicity boronated compounds and methods for their use in the treatment, visualization, and diagnosis of tumors. More specifically, the present invention is directed to low toxicity boronated 5, 10, 15, 20-tetraphenylporphyrin compounds and methods for their use particularly in boron neutron capture therapy (BNCT) or photodynamic therapy (PDT) for the treatment of tumors of the brain, head and neck, and surrounding tissue.

In particular, the present invention is directed to boron-containing 5, 10, 15, 20-tetraphenyl porphyrins of the formula

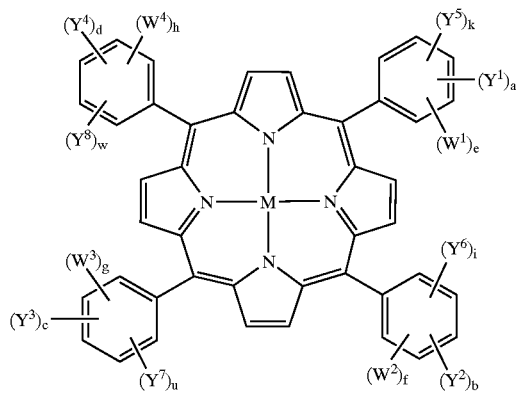

(1)

wherein:

$Y^1$, $Y^2$, $Y^3$, and $Y^4$ are independently on the ortho, meta or para position on the phenyl rings, and are independently hydrogen, alkyl, cycloalkyl, aryl, alkylaryl, arylalkyl, heteroaryl, or an alkyl, cycloalkyl, aryl, alkylaryl, arylalkyl, or heteroaryl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide; or a substituent represented by the formula

(2)

wherein D represents independently, Z, hydrogen, or a substituent represented by the formula

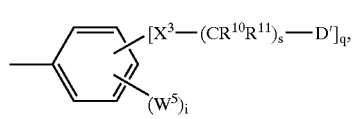

(3)

provided that at least one D is Z or is represented by formula (3);

wherein D' represents independently, Z, hydrogen, or a substituent represented by the formula

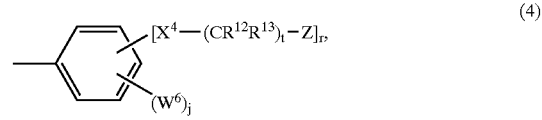

(4)

provided that when q is 0, or when q is not zero and D' is solely hydrogen, then at least one D is represented by Z, or when q is not zero and D' is represented by formula (4) and r is zero, then at least one D is represented by Z;

$Y^5$, $Y^6$, $Y^7$, and $Y^8$ are independently on the ortho, meta or para position on the phenyl rings, and are represented by the formula $$—X^a—(CR^aR^b)_v—Z \qquad (5);$$

$W^1$, $W^2$, $W^3$, $W^4$, $W^5$, and $W^6$ are hydrophilic groups independently on the ortho, meta or para position on the phenyl rings, and are independently selected from hydroxy, alkoxy, —C(O)OR$^5$, —SOR$^6$, —SO$_2$R$^6$, nitro, amido, ureido, carbamato, —SR$^7$, —NR$^8$R$^9$, or polyalkylene oxide;

$X^a$, $X^1$, $X^2$, $X^3$, and $X^4$ are independently oxygen or sulfur;

$R^a$, $R^b$, $R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from hydrogen and $C_1$ to $C_4$ alkyl;

Z is a carborane cluster comprising at least two carbon atoms and at least three boron atoms, or at least one carbon atom and at least five boron atoms, within a cage structure;

n, p, s, t, and v independently represent 0, or an integer from 1 to 20;

m independently represents 1, 2, or 3;

q and r independently represent 0, 1, 2, or 3;

a, b, c, and d independently represent 1 or 2;

k, l, u, and w independently represent 0, 1, or 2;

e, f, g, h, i, and j independently represent 0, or an integer from 1 to 5;

provided that at least one of $Y^1$, $Y^2$, $Y^3$, and $Y^4$ represents formula (2); each of the sums a+e+k, b+f+l, c+g+u, h+d+w, q+i, r+j, independently represents an integer from 1 to 5; when any of k, l, u, or w is not zero, then at least one of $Y^1$, $Y^2$, $Y^3$, and $Y^4$ represents formula (2); and M is either two hydrogen ions; a single monovalent metal ion; two monovalent metal ions; a divalent metal ion; a trivalent metal ion; a tetravalent metal ion; a pentavalent metal ion; a hexavalent metal ion; a radioactive metal ion useful in radioisotope-mediated radiation therapy or imageable by single photon emission computed tomography (SPECT) or positron emission tomography (PET); a paramagnetic metal ion detectable by magnetic resonance imaging (MRI); a metal ion suitable for boron neutron capture therapy (BNCT) or photodynamic therapy (PDT); or a combination thereof; wherein the porphyrin-metal complex derived from a single monovalent metal ion is charge-balanced by a counter cation, and the porphyrin-metal complex derived from a trivalent, tetravalent, pentavalent, hexavalent metal ion is charge-balanced by an appropriate number of counter anions, dianions, or trianions.

Z is preferably selected from the carboranes —C$_2$HB$_9$H$_{10}$ or —C$_2$HB$_{10}$H$_{10}$, wherein —C$_2$HB$_9$H$_{10}$ is ri do ortho-, meta-, or para-carborane, and —C$_2$HB$_{10}$H$_{10}$ is clo so ortho, meta-, or para-carborane.

M is preferably vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), or gadolinium (Gd). In a more preferred embodiment, M is copper (Cu) or nickel (Ni).

In one embodiment, a, b, c, and d are 1, $Y^1$, $Y^2$, $Y^3$, and $Y^4$ are represented by formula (2); D is Z; $X^1$ and $X^2$ are O; $R^1$, $R^2$, $R^3$ and $R^4$ are H; n and p are 1; m is 2; $Y^1$, $Y^2$, $Y^3$, and $Y^4$ are in the meta position on the phenyl ring; the —$X^2$—$(CR^3R^4)_p$—D substituents are in the 3 and 5, or 3 and 4, positions on the phenyl ring, and e, f, g, h, k, l, u, and w are 0.

In another embodiment, a, b, c, d, e, f, g, and h are 1; k, l, u, and w are 0; $Y^1$, $Y^2$, $Y^3$, and $Y^4$ are in the para position on the phenyl ring, $W^1$, $W^2$, $W^3$, and $W^4$ are in the meta position of the phenyl ring, $W^1$, $W^2$, $W^3$, and $W^4$ are independently, hydroxy or alkoxy, and the —$X^2$—$(CR^3R^4)_p$—D substituents are in the 3 and 5, or 3 and 4, positions of the phenyl ring, and D is Z. Preferably, alkoxy is methoxy.

In another embodiment, k, l, u, and w are 1; a, b, c, and d are 1, $Y^1$, $Y^2$, $Y^3$, and $Y^4$ are represented by formula (2); $X^1$ and $X^2$ are O; $R^1$, $R^2$, $R^3$ and $R^4$ are H; n and p are 1; and m is 2; $Y^1$, $Y^2$, $Y^3$, and $Y^4$ are in the meta position on the phenyl rings; $Y^5$, $Y^6$, $Y^7$, and $Y^8$ are in the para position on the phenyl rings; the —$X^2$—$(CR^3R^4)_p$—D substituents are in the 3 and 5, or 3 and 4, positions on the phenyl ring; D is Z; $X^a$ is O; $R^a$ and $R^b$ are H; v is 1, and e, f, g, and h are 0.

In yet another embodiment, a, b, c, and d are 2; $Y^1$, $Y^2$, $Y^3$, and $Y^4$ are represented by formula (2); $X^1$ and $X^2$ are O; $R^1$, $R^2$, $R^3$ and $R^4$ are H; n and p are 1; m is 2; $Y^1$, $Y^2$, $Y^3$, and $Y^4$ are in the meta positions on each phenyl ring; the —$X^2$—$(CR^3R^4)_p$—D substituents are in the 3 and 5, or 3 and 4, positions on the phenyl ring; D is Z; k, l, u, and w are 0; and e, f, g, and h are 0.

In yet another embodiment, a, b, c, and d are 1; e, f, g, h, k, l, u, and w are 0; $Y^1$, $Y^2$, $Y^3$, and $Y^4$ are represented by formula (2); $X^1$ and $X^2$ are O; $R^1$, $R^2$, $R^3$ and $R^4$ are H; n and p are 1; m is 2; $Y^1$, $Y^2$, $Y^3$, and $Y^4$ are in a meta position on each phenyl ring; the —$X^2$—$(CR^3R^4)_p$—D substituents are in the 3 and 5, or 3 and 4, positions on the phenyl ring; D is according to formula (3), wherein $X^3$ is O, $R^{10}$ and $R^{11}$ are H, s is 1, D' is Z, q is 2, and i is 0. Since i is 0, $W^5$ is not present.

In yet another embodiment, when the porphyrin compound requires a counter dianion, the counter dianion is a porphyrin compound containing a divalent negative charge. The porphyrin compound containing a divalent negative charge may be a carborane-containing porphyrin compound of the present invention, with the proviso that M is absent.

The present invention also includes methods of tumor imaging by SPECT, PET, or MRI, as well as methods of bimodal cancer treatment such as BNCT and PDT that require the administration to a subject of a composition that comprises one or more of the porphyrin compounds described above. In a preferred embodiment, the composition is essentially one or more of the porphyrin compounds described above.

DETAILED DESCRIPTION OF THE INVENTION

The invention relates to boron-containing 5, 10, 15, 20-tetraphenyl porphyrins having the formula

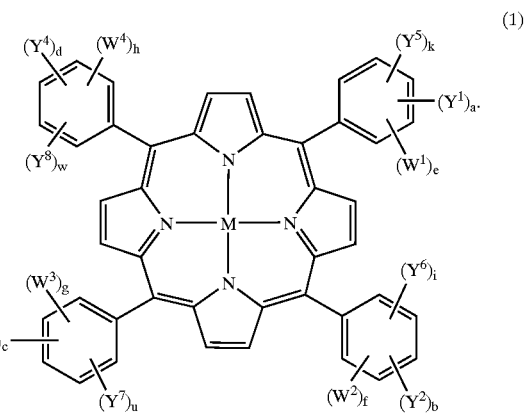

$Y^1$, $Y^2$, $Y^3$, and $Y^4$ are independently on the ortho, meta or para position on the phenyl rings, and a, b, c, and d independently represent 1 or 2. $Y^1$, $Y^2$, $Y^3$, and $Y^4$ are independently hydrogen, alkyl, cycloalkyl, aryl, alkylaryl, arylalkyl, heteroaryl, or an alkyl, cycloalkyl, aryl, alkylaryl, arylalkyl, or heteroaryl group substituted with 1 to 4 hydrophilic groups selected from hydroxy, alkoxy, —C(O)$OR^5$, —$SOR^6$, —$SO_2R^6$, nitro, amido, ureido, carbamato, —$SR^7$, —$NR^8R^9$, or poly-alkyleneoxide; or a substituent represented by the formula

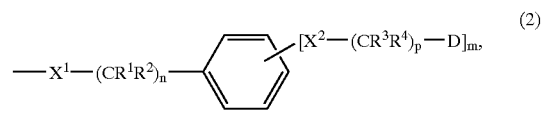

provided that at least one of $Y^1$, $Y^2$, $Y^3$, and $Y^4$ represents formula (2).

In formula (2), $X^1$ and $X^2$ are independently oxygen or sulfur, and $R^1$, $R^2$, $R^3$, and $R^4$ are independently selected from hydrogen and alkyl groups as defined below, except that the alkyl groups for $R^1$, $R^2$, $R^3$, and $R^4$ contain 1 to 4 carbon atoms. The subscripts n and p independently represent 0, or an integer from 1 to 20, and m independently represents 1, 2, or 3.

D represents independently, Z, hydrogen, or a substituent represented by the formula

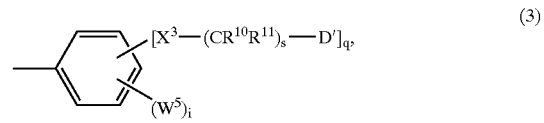

provided that at least one D is Z or is represented by formula (3).

In formula (3), $X^3$ is independently oxygen or sulfur; $R^{10}$ and $R^{11}$ are independently selected from hydrogen and alkyl groups as defined below, except that the alkyl groups for $R^{10}$ and $R^{11}$ contain 1 to 4 carbon atoms; s independently represents 0, or an integer from 1 to 20; and q independently represents 0, 1, 2, or 3, provided that when q is 0, or when q is not zero and D' is solely hydrogen, then at least one D is represented by Z, or when q is not zero and D' is represented by formula (4) and r is zero, then at least one D is represented by Z.

D' represents independently, Z, hydrogen, or a substituent represented by the formula

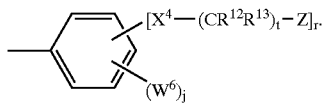

(4)

In formula (4), $X^4$ is independently oxygen or sulfur; $R^{12}$ and $R^{13}$ are independently selected from hydrogen and alkyl groups as defined below, except that the alkyl groups for $R^{12}$ and $R^{13}$ contain 1 to 4 carbon atoms; t independently represents 0, or an integer from 1 to 20; and r independently represents 0, 1, 2, or 3.

Z is a carborane cluster comprising at least two carbon atoms and at least three boron atoms, or at least one carbon atom and at least five boron atoms, within a cage structure. Some examples of carborane clusters include the regular polyhedral carborane clusters, also known as clo so structures, as well as ionized fragments of the polyhedral clusters, also known as ri do structures. Some examples of the preferred carboranes of the present invention include —$C_2HB_9H_{10}$ or —$C_2HB_{10}H_{10}$, wherein —$C_2HB_9H_{10}$ is ri do ortho-, meta-, or para-carborane, and —$C_2HB_{10}H_{10}$ is clo so ortho-, meta-, or para-carborane.

$W^1$, $W^2$, $W^3$, $W^4$, $W^5$, and $W^6$ are hydrophilic groups independently on the ortho, meta or para position on the phenyl rings. $W^1$, $W^2$, $W^3$, $W^4$, $W^5$, and $W^6$ are independently selected from hydroxy, alkoxy, —$C(O)OR^5$, —$SOR^6$, —$SO_2R^6$, nitro, amido, ureido, carbamato, —$SR^7$, —$NR^8R^9$, or polyalkylene oxide. $R^5$, $R^6$, $R^7$, $R^8$, $R^9$, are independently selected from hydrogen and alkyl groups as defined below, except that the alkyl groups for $R^5$, $R^6$, $R^7$, $R^8$, $R^9$ contain 1 to 4 carbon atoms. The subscripts e, f, g, h, i, and j independently represent 0, or an integer from 1 to 5.

$Y^5$, $Y^6$, $Y^7$, and $Y^8$ are independently on the ortho, meta or para position on the phenyl rings, and are represented by the formula —$X^a$—$(CR^aR^b)_v$—Z (5). In formula 5, $X^a$ is independently oxygen or sulfur; $R^a$ and $R^b$ are independently selected from hydrogen and alkyl groups as defined below, except that the alkyl groups for $R^a$ and $R^b$ contain 1 to 4 carbon atoms; v independently represents 0, or an integer from 1 to 20; k, l, u, and w independently represent 0, 1, or 2; provided that each of the sums a+e+k, b+f+l, c+g+u, h+d+w, q+i, r+j, independently represents an integer from 1 to 5; when any of k, l, u, or w is not zero, then at least one of $Y^1$, $Y^2$, $Y^3$, and $Y^4$ represents formula (2).

When any of $Y^1$, $Y^2$, $Y^3$, or $Y^4$ is alkyl, alkyl is a straight chain or branched alkyl group containing 1 to 20 carbon atoms including, optionally, up to three double or triple bonds. Some examples of alkyl groups include methyl, ethyl, n-propyl, iso-propyl, n-butyl, iso-butyl, sec-butyl, tert-butyl, propenyl, 2-butenyl, 3-butenyl, 3-butynyl, 2-methyl-2-butenyl, n-pentyl, dodecyl, hexadecyl, octadecyl, and eicosyl.

The alkyl group may be unsubstituted or substituted with 1 to 4 hydrophilic groups. Some examples of suitable hydrophilic groups include hydroxy, alkoxy, —$C(O)OR^5$, —$SOR^6$, —$SO_2R^6$, nitro, amido, ureido, carbamato, —$SR^7$, —$NR^8R^9$, and poly-alkyleneoxide. $R^5$, $R^6$, $R^7$, $R^8$, and $R^9$ are independently selected from hydrogen and alkyl groups as defined above, except that the alkyl groups for $R^5$, $R^6$, $R^7$, $R^8$ contain 1 to 4 carbon atoms.

The carbon atoms of the alkyl group may also be substituted with 1 to 4 heteroatoms. In this specification, heteroatoms are O, N, or S. The heteroatoms are not adjacent, and are separated by at least one carbon atom.

When any of $Y^1$, $Y^2$, $Y^3$, or $Y^4$ is cycloalkyl, the cycloalkyl ring is a 4, 5, 6, or 7 member cycloalkyl ring. The ring may be saturated, or may contain 1 to 4 unsaturated (i.e., double or triple) bonds. Some examples of saturated cycloalkyl rings include cyclobutane, cyclopentane, cyclohexane, and cyclopentane rings. Some examples of unsaturated cycloalkyl rings include cyclobutene, cyclopentene, cyclohexene, and 1,3-cycloheptadiene rings.

The cycloalkyl ring may optionally be substituted with 1 to 4 heteroatoms of O, N, or S. Some examples of cycloalkyl rings substituted with heteroatoms include pyrrolidine, piperidine, piperazine, tetrahydrofuran, furan, thiophene, 1,3-oxazolidine, imidazole, and pyrrole rings. The cycloalkyl rings may be optionally substituted with alkyl as defined above, or with 1 to 4 hydrophilic groups, also as defined above.

The cycloalkyl ring may be fused to 1 to 3 additional 4, 5, 6, or 7 member cycloalkyl or phenyl rings. Some examples of fused cycloalkyl rings are bicyclo[3.3.0]octane, bicyclo[4.3.0]non-3-ene, triphenylene, and 1,2,3,4-tetrahydronaphthalene rings.

When any of $Y^1$, $Y^2$, $Y^3$, or $Y^4$ is aryl, aryl is a 5, 6, or 7 member aromatic ring, preferably a phenyl ring. The aryl rings may be optionally substituted with alkyl as defined above to produce alkylaryl or arylalkyl groups. The aryl, alkylaryl, and arylalkyl groups may be substituted with 1 to 4 hydrophilic groups, as defined above.

The aryl ring may optionally be substituted with 1 to 4 heteroatoms of O, N, or S, resulting in a heteroaryl ring. Some examples of heteroaryl rings include thiophene, pyridine, oxazole, thiazole, oxazine, and pyrazine rings. The heteroaryl ring may be substituted with 1 to 4 hydrophilic groups, as defined above.

The aryl or heteroaryl ring may also be fused to 1 to 3 additional 5, 6, or 7 member aryl or heteroaryl rings. Some examples of fused aryl and heteroaryl rings include napthalene, anthracene, phenanthrene, triphenylene, chrysene, indoline, quinoline, and tetraazanaphthalene (pteridine) rings.

In this specification, an alkoxy group contains an alkyl portion as defined above. Some examples of alkoxy groups include methoxy, ethoxy, propoxy, n-butoxy, t-butoxy, and dodecyloxy.

A polyalkylene oxide is defined according to the formula —$(CH_2)_d$—O—[$(CH_2)_e$—O—]$_x$—[$(CH_2)_f$—O—]$_y$—$(CH_2)_g$—OR', wherein, independently, d is 0, or an integer from 1 to 10, e is 0, or an integer from 1 to 10, f is 1 to 10, g is 1 to 10, x and y are each independently 1 or 0, and R' is either H or an alkyl group as defined previously, provided that when e is 0, then x is 0; when f is 0, then y is 0; when e is not 0, then x is 1; and when f is not 0, then y is 1.

A preferable polyalkylene oxide of the invention is polyethylene oxide. Polyethylene oxide is defined according to the formula —$(CH_2)_d$—O—[$(CH_2)_e$—O—]$_x$[$(CH_2)_f$—O—]$_y$ —$(CH_2)_g$—OR', wherein, independently, d is 0 or 2, e is 0 or 2, f is 0 or 2, g is 2, x and y are each independently 1 or 0, and R' is either H or an ethyl group, provided that when e is 0, then x is 0; when f is 0, then y is 0; when e is not 0, then x is 1; and when f is not 0, then y is 1.

In formula (1), M may be two hydrogen ions, a single monovalent metal ion, or two monovalent metal ions. Some examples of suitable monovalent metal ions include $Li^{+1}$, $Na^{+1}$, $K^{+1}$, $Cu^{+1}$, $Ag^{+1}$, $Au^{+1}$, and $Tl^{+1}$. When M is a single monovalent metal ion, the resulting porphyrin-metal complex anion is charge-balanced by a counter cation. Some examples of counter cations include any of the foregoing monovalent metal ions, and ammonium and phosphonium cations, such as tetramethylammonium, tetrabutylammonium, and tetraphenylammonium. The counter cation may be either bound or associated in some form with the porphyrin-metal complex.

M may also be a divalent metal ion. Some examples of suitable divalent metal ions include $V^{+2}$, $Mn^{+2}$, $Fe^{+2}$, $Co^{+2}$, $Ni^{+2}$, $Cu^{+2}$, $Pd^{+2}$, $Pt^{+2}$, $Zn^{+2}$, $Ca^{+2}$, $Mg^{+2}$, $Sr^{+2}$, and $Ba^{+2}$.

Alternatively, M may be a trivalent, tetravalent, pentavalent, or hexavalent metal ion. Some examples of suitable trivalent metal ions include $Gd^{+3}$, $Y^{+3}$, $In^{+3}$, $Cr^{+3}$, $Ga^{+3}$, $Al^{+3}$, $Eu^{+3}$, and $Dy^{+3}$. Some examples of suitable tetravalent metal ions include $Tc^{+4}$, $Ge^{+4}$, $Sn^{+4}$, and $Pt^{+4}$. An example of a suitable pentavalent metal ion is $Tc^{+5}$. Some examples of suitable hexavalent metal ions include $W^{+6}$, $T^{+6}$, and $Mo^{+6}$. The resulting porphyrin-metal complex cation is charge-balanced by an appropriate number of counter anions, dianions, or trianions. For example, a porphyrin-metal complex cation derived from a trivalent metal ion may be charge-balanced by a single counter anion, and such a complex derived from a tetravalent metal ion may, for example, be charge-balanced by a single counter dianion or two counter anions, and so on.

Some examples of suitable counter anions include chloride, perchlorate, sulfate, nitrate, and tetrafluoroborate. Some examples of suitable counter dianions include oxide, sulfide, or a porphyrin compound containing a divalent negative charge. The porphyrin compound containing a divalent negative charge may be a porphyrin compound of the present invention with the proviso that M is absent. An example of a suitable counter trianion includes phosphate.

The counter anion, dianion, or trianion may be either bound or associated in some form with a carborane-containing porphyrin compound of the present invention. The carborane-containing porphyrin compound may also be bound to or associated with neutrally charged molecules, such as molecules of solvation, for example, water, acetonitrile, methanol, and so on.

In addition, M may be a radioactive metal ion imageable by single photon emission computed tomography (SPECT) or positron emission tomography (PET). Some examples of radioactive metals suitable for SPECT are $^{67}Cu$, $^{99}Tc$, $^{11}In$, and those for PET include $^{64}Cu$, $^{55}Co$. M may also be a radioactive metal useful as a radiopharmaceutical for therapy. Some examples of radioactive metals suitable for such therapy include $^{90}Y$, $^{188}Re$, $^{67}Cu$.

M may also be a paramagnetic metal ion detectable by magnetic resonance imaging (MRI). Some examples of such metals include Mn, Fe, Co, and Gd.

In addition, M may be a metal ion suitable for boron neutron capture therapy (BNCT) or photodynamic therapy (PDT); or a combination thereof. The metal ions suitable for BNCT include those described thus far, with the exclusion of those that are photoactive, such as Zn and Sn. Such photoactive metals, and particularly those with long-lived triplet states, are preferable for PDT. Since the dosage for BNCT is 100 to 1000 times greater than the dosage for PDT, a significant accumulation of photoactive metal in the skin could result if such photoactive metals were used in BNCT. Such an accumulation of photoactive metal may cause biological damage.

The invention also relates to methods of treating tumors. In a preferred embodiment, the method of treating malignant tumors, especially brain tumors, is via BNCT. BNCT is a bimodal cancer treatment based on the selective accumulation of a stable nuclide of boron known as boron-10, or $^{10}B$, in the tumor, followed by irradiation of the tumor with thermalized neutrons. The thermalized neutrons impinge on the boron-10, causing a nuclear fission reaction. The nuclear fission causes the highly localized release of vast amounts of energy in the form of high linear-energy-transfer (LET) radiation, which can more effectively kill cells than low LET radiation, such as x-rays.

Boron-10 undergoes the following nuclear reaction when captured by a thermal neutron:

$$^{10}B + n \rightarrow {}^{11}B$$

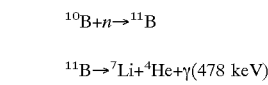

In this nuclear reaction, a boron-10 nucleus captures a neutron forming the metastable nuclide $^{11}B$, which spontaneously and nearly instantaneously disintegrates into a $^{4}He$ and $^{7}Li$ particle, which together possess an average total kinetic energy of 2.34 MeV. These two ionized particles travel about 9 μm and 5 μm (7±2 μm) in opposite directions in soft tissue, respectively.

The distances traveled by the $^{4}He$ and $^{7}Li$ particles are comparable to the diameter of many tumor and tumor-associated cells. Therefore, the efficacy of BNCT resides in the production of highly localized, high LET ionizing radiation within the tumor. The targeted tumor thus receives a large dose of radiation while sparing surrounding normal tissue.

In the case of brain tumors, after administration of the boron compound, the patient's head is irradiated in the general area of the brain tumor with an incident beam or field of epithermal (0.5 eV–10 keV) neutrons. The neutrons become progressively thermalized (average energy approximately 0.04 eV) as they penetrate deeper into the head. As the neutrons become thermalized, they are more readily captured by the boron-10 concentrated in the tumor cells and/or tumor supporting tissues, since the capture cross section is inversely proportional to the neutron velocity.

In BNCT of malignant brain tumors following the method of the present invention, the patient is first given an infusion of a carborane-containing porphyrin of formula (1), which is highly enriched in boron-10. The carborane-containing porphyrin is then concentrated preferentially in the brain tumor within the effective irradiation volume, which, for brain tumors may be a substantial part of the brain. For example, tumors located in most or all of one hemisphere and some or all of the contralateral hemisphere of the brain can accumulate boronated porphyrins.

The tumor area is then irradiated with thermalized neutrons (primary irradiation), some of which are captured by the boron-10 concentrated in the tumor. The relative probability that the slow-moving thermal neutrons will be captured by the boron-10 nuclide is high compared to the probability of capture by all of the other nuclides normally present in mammalian tissues, provided that boron-10 concentrations in tumor tissues is greater than 30 μg/g.

Since a minuscule proportion of the boron-10 nuclei in and around a tumor undergoes the nuclear reaction immediately after capturing a neutron, a high concentration of boron-10 in the targeted tissue is necessary for BNCT to be clinically effective. Therefore, to maximize the concentration of boron-10 in the targeted tissue, the carborane clusters are highly enriched in boron-10. Specifically, the boron in the carborane cluster is enriched to at least 95 atom % in boron-10.

An advantage of the present invention over the prior art for the treatment of cancer is that the boron-containing porphyrins of the present invention selectively accumulate in neoplasms in more preferred ratios than other known boron-containing compounds.

Additionally, the porphyrin compounds of the present invention that have been tested in vivo are non-toxic at theoretically therapeutic effective doses. The higher selectivity and lower toxicity of the carborane-containing porphyrins of the present invention allow for the selective destruction of tumor tissue with minimal disruption of normal tissues and tissue function when irradiated.

Another advantage of the carborane-containing porphyrins of the present invention is their increased polarity, imparted by the hydrophilic groups $W^1$, $W^2$, $W^3$, $W^4$, $W^5$, and $W^6$, and/or the ether linkages. The greater polarity of such groups render the tetraphenyl porphyrin compounds less lipophilic, which effects a reduction of the amount of an emulsifying co-solvent during administration. Therefore, the microlocalization within the tumor cell may be improved yielding a higher relative biological effect.

In addition, the ether linkages in the carborane-containing porphyrins of the present invention provide more chemical stability than, for example, ester or amide linkages, which can much more easily hydrolyze, thereby causing the loss of the boron functionality. In fact, the ether linkages possess nearly the same resistance to hydrolysis and other forms of chemical attack as a carbon-carbon linkage.

It is significant that some of the preferred carborane-containing porphyrins of the present invention contain in excess of 8 carborane clusters (80 boron atoms). In fact, the present invention provides for carborane-containing porphyrin molecules containing in excess of 16, 32, or even 64, carborane clusters, which is higher than any carborane-containing porphyrins currently known.

Since such high carborane-containing porphyrin molecules deliver more boron to a target, i.e., are more potent, they permit lower required molar doses of porphyrin as compared to the porphyrin compounds in the prior art. The lower molar dose of carborane-containing porphyrin allows the amount of boron at the target to be significantly increased while keeping blood porphyrin concentrations well below toxic threshold values.

To accumulate the requisite amount of a compound of the present invention in a tumor, generally a systemically injected or infused dose of about 10–50 milligrams of boron-10 per kg body weight in a pharmaceutically acceptable carrier is administered to a patient. The carrier may include such commercially available solvents as Cremophor EL, propylene glycol, Tween 80, polyethylene glycol, or liposomes. The compound is administered in one or more doses, the last dose being given between about 1 hour and one week prior to the epithermal neutron irradiation.

The timing of the neutron exposure depends upon the concentration of the porphyrin in the blood, which decreases more rapidly with time than the porphyrin concentration in the tumor. The timing of the neutron exposure also depends on other factors that are well known to those skilled in the art of clinical BNCT. These other factors include the pharmacokinetic behavior of the compound, (e.g., the rate of absorption of the compound into the tumor and into the tumor vasculature) and the rate of excretion from and/or metabolism of the compound in the tumor and various other tissues that absorb the compound.

In another preferred embodiment, the method of treating malignant tumors of the present invention is via PDT. PDT is a bimodal cancer treatment based on the selective accumulation of a porphyrin in a tumor, followed by irradiation of the tumor with laser red light. Upon activation with light, an electron of the porphyrin is excited from the singlet ground state to a singlet excited state. The electron then can either return to the singlet ground state with the emission of light causing fluorescence, or it can change its spin via intersystem crossing to the triplet state. In the decay of the triplet back down to the ground state singlet, it can transfer energy to ground state triplet dioxygen which forms the highly reactive singlet oxygen. Biomolecules that react most readily with singlet oxygen include unsaturated lipids and alpha amino-acid residues, both of which are major constituents of biological membranes. Beyond a certain reversible or repairable threshold, damage to membranes, especially to endothelial cell membranes, can lead to local vascular thrombosis and shutdown of blood circulation.

In using PDT in the present invention, the patient is first given an injection or infusion of a photosensitizing carborane-containing porphyrin of formula (1). Fiber-optic probes are then used to illuminate the tumor tissue. For malignant tumors, it is preferable that the PDT photosensitizers have optical absorbance peaks at sufficiently long wavelengths for maximum penetration to the depth of the tumor.

In a preferred embodiment, the therapeutic treatment of malignant tumors is augmented by the use of SPECT or PET. In SPECT, the patient is first given an infusion or injection of a compound of formula (1) wherein M is a gamma-emitting radioactive metal ion. The patient's head is then scanned noninvasively and the radionuclide concentration, and hence indirectly, the average boron concentration, in each pixel or voxel representing brain or brain tumor tissue is imaged. Contour lines representing zones of equal boron-10 concentration can thereby be drawn on each image of the brain.

SPECT of the brain is at least one order of magnitude more sensitive to isotopic tracers than is conventional radiography or computerized tomography. In addition, SPECT results, as opposed to results from conventional radiography, can be analyzed to provide quantitative information either in defined volumes or voxels of the brain images, in the concentrations of boron relevant to BNCT treatment planning and implementation. SPECT scanning can indicate the presence of a tumor in the patient, as well as its location in the brain or elsewhere in the body. SPECT scanning is noninvasive, fast, and convenient.

However, the positron emitting PET-imageable radioisotope Cu-64, is more readily available than is Cu-67, used in SPECT. Because of the much greater availability of Cu-64, we have carried out preclinical PET studies using a Cu-64 labeled porphyrin.

In another preferred embodiment, the therapeutic treatment of malignant tumors is augmented by the use of MRI. In MRI, a patient is first given an infusion or injection of a solution containing a carborane-containing porphyrin of formula (I) chelated to a suitable paramagnetic metal ion. For a brain tumor, the patient's head is then scanned and the paramagnetic metal ion concentration, and thus, boron concentration in the brain is imaged and quantified. MRI utilizing the compounds of the present invention may permit rapid enhanced targeting and treatment planning for neutron irradiation in BNCT before, during and after infusion when the boronated compound is being redistributed in blood, tumor, and healthy tissue.

The carborane-containing porphyrins of the present invention are synthesized through a series of separate steps. Provided below is first, a summary of the synthetic steps required for the preparation of the preferred carborane-containing porphyrins of the present invention. The synthetic summary provides general methods for synthesizing compounds of the invention, and is thereby meant to encompass numerous ways for synthesizing each compound. For example, different starting materials may be used to synthesize the same product, and each starting material may require a different set of reaction conditions such as temperature, reaction time, solvents, and extraction and purification procedures.

The specific examples describe a preferred method for synthesizing the compounds of the present invention. The scope of this invention is not to be in any way limited by the examples set forth herein. For example, assymmetric carborane-containing tetraphenylporphyrin compounds can be synthesized by using a mixture of different benzaldehyde or dibenzaldehyde starting materials and proceeding with a similar synthetic reaction as shown in Reaction Scheme 8.

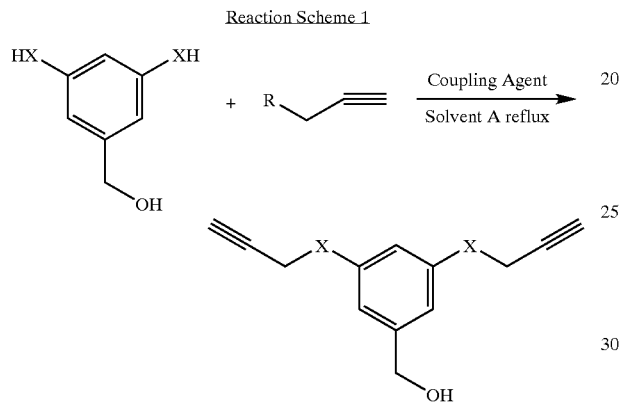

where X is either O or S, solvent A is preferably a polar non-protic solvent such as acetone, and R is a halogen, preferably Cl. The coupling agent is any compound, mixture, or sequence of compounds capable of coupling a phenol or thiophenol and an alkyl halide to produce an ether. Some coupling agents may not require reflux conditions or a polar non-protic solvent. Preferably, the coupling agent is a mixture of potassium carbonate and potassium iodide ($K_2CO_3/KI$).

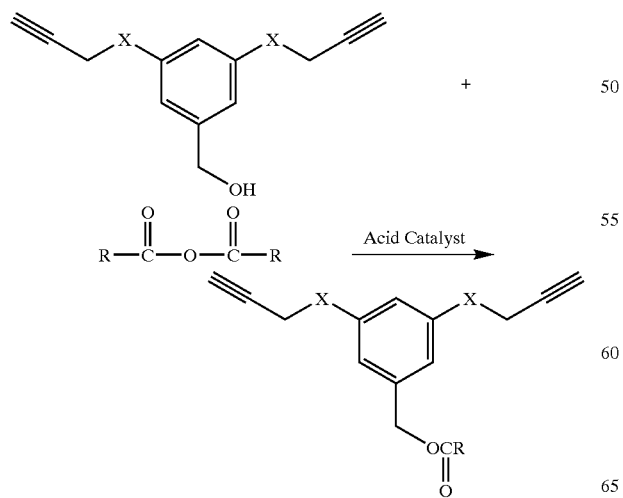

where X is either O or S, and the R groups on the anhydride may be the same or different, and selected from alkyl, cycloalkyl or aryl. A preferred anhydride is acetic anhydride wherein R is methyl. The acid catalyst may be any Bronsted-Lowry (proton donating) acid that does not interfere with conversion of the alcohol to the ester product. Preferably, the acid catalyst is sulfuric acid, $H_2SO_4$.

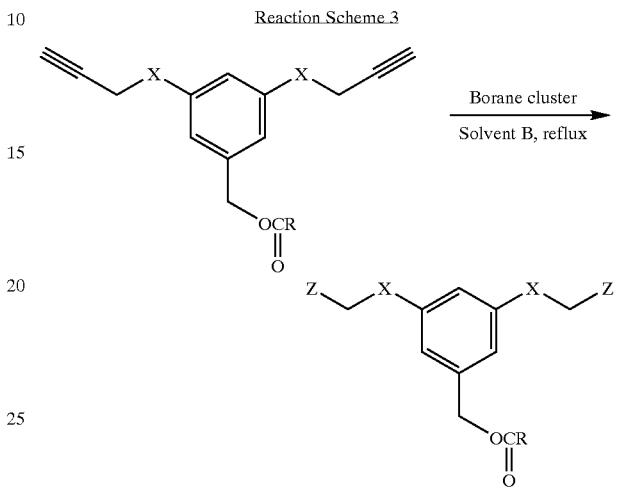

where X is either O or S, solvent B is preferably a polar, aprotic solvent, preferably acetonitrile, and R is as defined in reaction scheme 2. The borane cluster is any cluster comprising at least three boron atoms within a cage structure. For example, the borane cluster can be decaborane, $B_{10}H_{14}$. The borane cluster reacts with the triple bond of the propargyl starting material to form the carboranyl product. Thus, in the case of decaborane, Z represents the carborane —$C_2HB_{10}H_{10}$. Z represents any carborane cluster comprising at least two carbon atoms and at least three boron atoms, or at least one carbon atom and at least five boron atoms, within a cage structure. For example, the carborane cluster may be —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

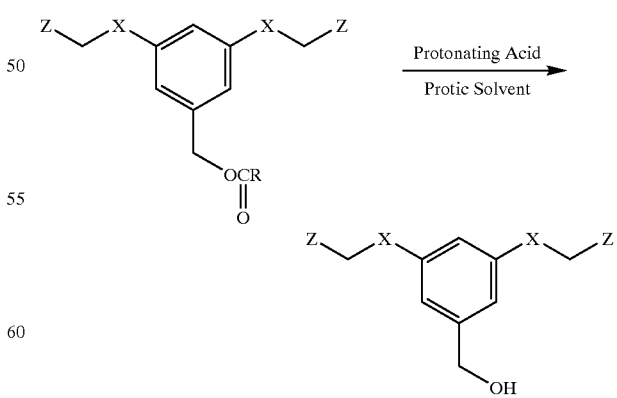

where X, R, and Z are as defined above. The protonating acid is any acid, acid mixture, or sequence of acid additions capable of converting the ester into the alcohol product.

Preferably, the protonating acid is concentrated HCl. The protic solvent may be, for example, an alcohol such as methanol.

Reaction Scheme 5

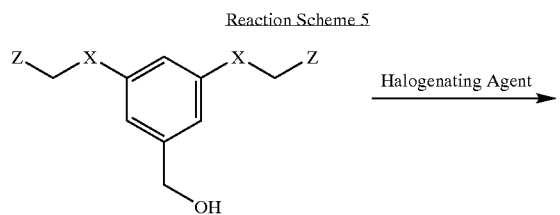

where X and Z are as defined above, and D is a halogen. The halogenating agent is any agent capable of converting the hydroxy substituent of the starting material to a halogen. Preferably, the halogenating agent is a 1:1 mixture of carbon tetrabromide and triphenylphosphine, wherein D becomes a bromide. The reaction is performed preferably in an ether solvent, such as tetrahydrofuran (THF).

Reaction Scheme 6

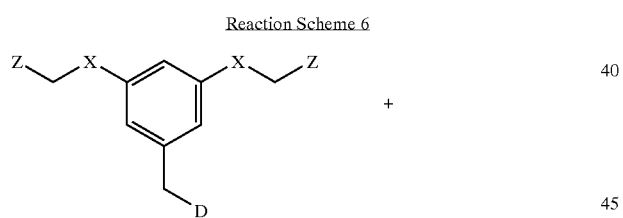

where X, Z, and D are as defined previously. Solvent C is preferably a polar, aprotic solvent such as acetone. The coupling agent is any compound, mixture, or sequence of compounds capable of coupling a phenol or thiophenol and an alkyl halide to produce an ether. Some coupling agents may not require reflux conditions or a polar, aprotic solvent. Preferably, the coupling agent is a mixture of potassium carbonate and potassium iodide (K$_2$CO$_3$/KI).

Reaction Scheme 7

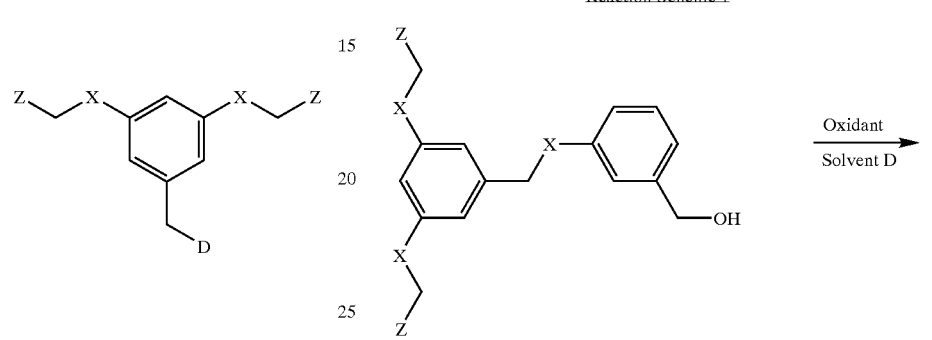

where X and Z are as previously defined. The oxidant is any oxidizing compound capable of selectively converting a primary alcohol to an aldehyde, preferably 2,3-dichloro-5,6-dicyano-1,4-benzoquinone (DDQ) or pyridinium chlorochromate (PCC). Solvent D is a non-polar aprotic solvent, preferably dichloromethane.

Reaction Scheme 8

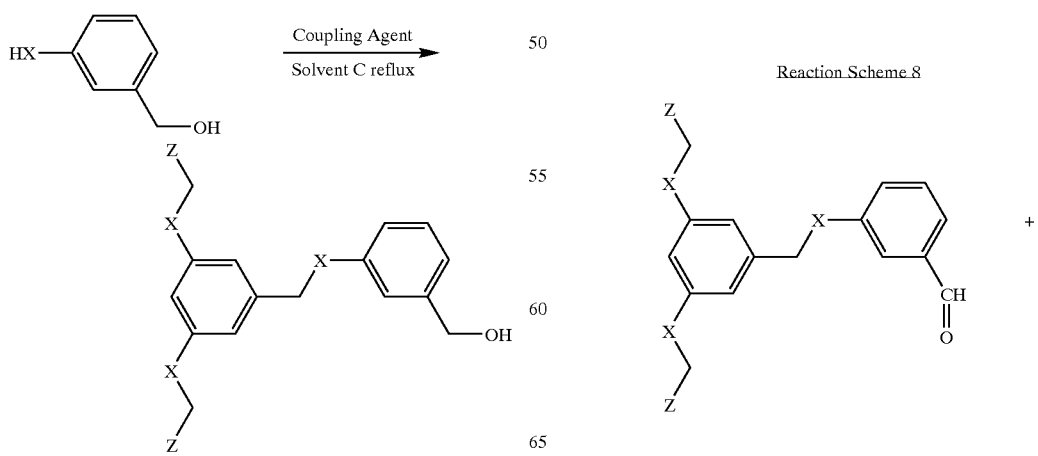

-continued

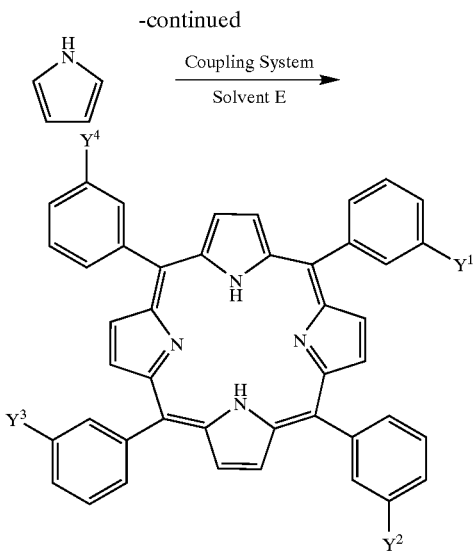

wherein $Y^1$, $Y^2$, $Y^3$, and $Y^4$ are represented by

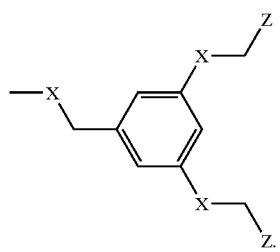

X and Z have been previously defined. The coupling system preferably comprises a Lewis acid (electron acceptor) such as boron trifluoride ($BF_3$) or trifluoroacetic acid (TFA) to form the intermediate porphyrinogen from the pyrrole, and benzaldehyde and an oxidizing agent such as 2,3-dichloro-5,6-dicyano-1.4-benzoquinone (DDQ) to oxidize the porphyrinogen to porphyrin. Solvent E is a nonpolar aprotic solvent, preferably dichloromethane.

Reaction Scheme 9

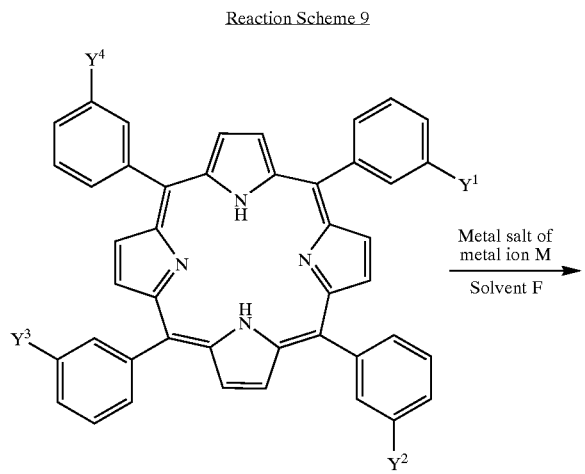

-continued

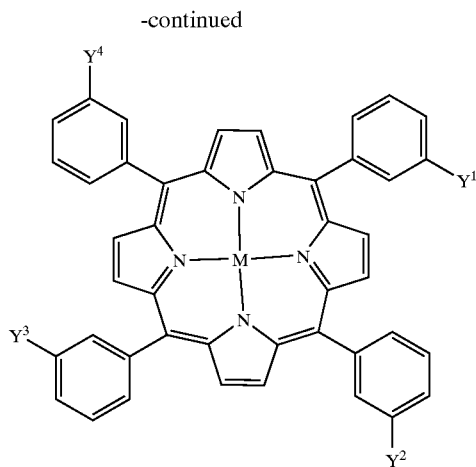

where $Y^1$, $Y^2$, $Y^3$, and $Y^4$ are as defined above. In a preferred embodiment, M is selected from the group consisting of vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), and gadolinium (Gd). In a more preferred embodiment, M is copper (Cu) or nickel (Ni). The metal salt used contains the metal ion M chelated to the porphyrin. For example, for the compound where M is desired to be copper, copper acetate, i.e., $Cu(OAc)_2 \cdot H_2O$, may be used as the metal salt. Solvent F is any solvent or solvent mixture capable of at least partially solubilizing the porphyrin and metal salt, and that does not interfere with incorporating the metal into the porphyrin.

For example, using schemes 1–8, and as will be seen through examples 1–8, the 8-carborane-containing porphyrin, i.e., porphyrin (VIII), has been prepared. Porphyrin VIII has the following structure:

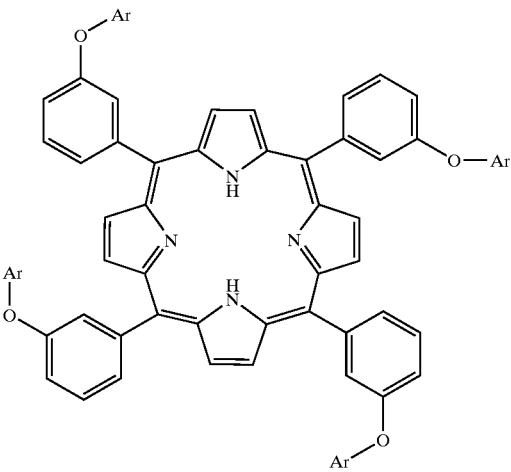

-continued

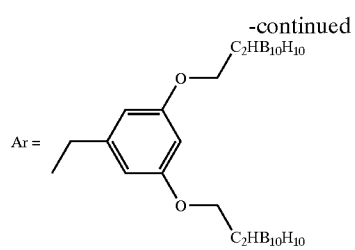

Porphyrin VIII shown above. In this case, a, b, c, and d are 1, $Y^1$, $Y^2$, $Y^3$, and $Y^4$ are represented by formula (2); D is Z, wherein Z is the —$C_2HB_{10}H_{10}$ carborane; $X^1$ and $X^2$ are O; $R^1$, $R^2$, $R^3$ and $R^4$ are H; n and p are 1; m is 2; $Y^1$, $Y^2$, $Y^3$, and $Y^4$ are in the meta position on the phenyl ring; the —$X^2$—$(CR^3R^4)_p$—D substituents are in the 3 and 5 positions on the phenyl ring, and e, f, g, h, k, l, u, and w are 0.

Using similar reaction schemes as shown above, the inventors predict facile syntheses of Porphyrins A, B, C, and D, which are shown below. In fact, starting materials for each of these porphyrin compounds have either already been synthesized or are presently in the process of being synthesized.

Porphyrin A, an 8-carborane-containing porphyrin containing hydrophilic groups $W^1$, $W^2$, $W^3$, and $W^4$:

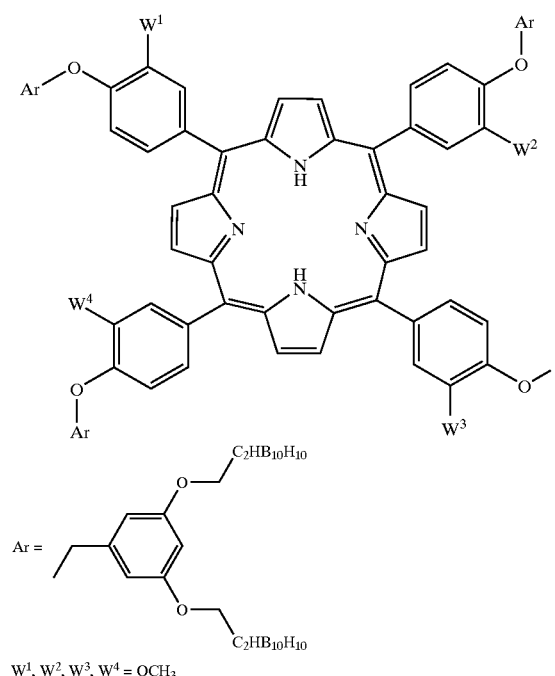

$W^1$, $W^2$, $W^3$, $W^4$ = $OCH_3$

In the case of Porphyrin A above, a, b, c, d, e, f, g, and h are 1; k, l, u, and w are 0; $Y^1$, $Y^2$, $Y^3$, and $Y^4$ (i.e., O—Ar) are in the para position of each phenyl ring, the hydrophilic groups $W^1$, $W^2$, $W^3$, and $W^4$ are in the meta position of each phenyl ring, wherein $W^1$, $W^2$, $W^3$, and $W^4$ are methoxy; the —$X^2$—$(CR^3R^4)_p$—D substituents are in the 3 and 5 positions of the Ar phenyl rings; D is Z, wherein Z is the —$C_2HB_{10}H_{10}$ carborane.

Porphyrin B, a 12-carborane-containing porphyrin:

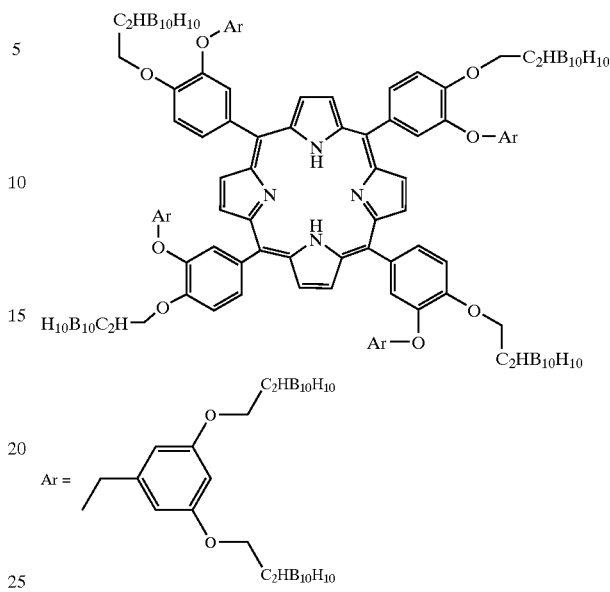

In the case of Porphyrin B above, k, l, u, and w are 1; a, b, c, and d are 1, $Y^1$, $Y^2$, $Y^3$, and $Y^4$ are represented by formula (2); $X^1$ and $X^2$ are O; $R^1$, $R^2$, $R^3$ and $R^4$ are H; n and p are 1; and m is 2; $Y^1$, $Y^2$, $Y^3$, and $Y^4$ (i.e., O—Ar) are in the meta position of each phenyl ring; $Y^5$, $Y^1$, $y^7$, and $Y^8$ (in this case, O—$CH_2$—$C_2HB_{10}H_{10}$) are in the para position of each phenyl ring; the —$X^2$—$(CR^3R^4)_p$—D substituents are in the 3 and 5 positions of the Ar phenyl rings; D is Z, wherein Z is the —$C_2HB_{10}H_{10}$ carborane; $X^a$ is O; $R^a$ and $R^b$ are H; v is 1, and e, f, g, and h are 0.

Porphyrin C, an 8-carborane-containing porphyrin:

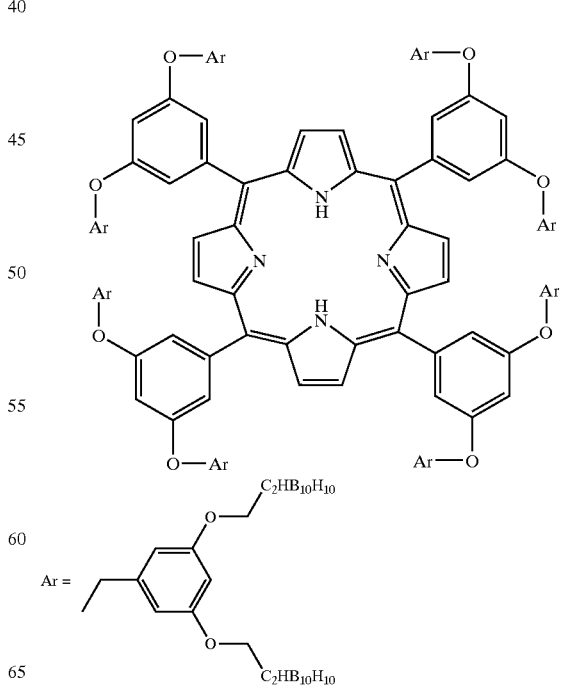

In the case of Porphyrin C above, a, b, c, and d are 2; $Y^1$, $Y^2$ $Y^3$, and $Y^4$ (i.e., O—Ar) are represented by formula (2); $X^1$ and $X^2$ are O; $R^1$, $R^2$, $R^3$ and $R^4$ are H; n and p are 1; m is 2; $Y^1$, $Y^2$ $Y^3$, and $Y^4$ are in the two meta positions on each phenyl ring; the —$X^2$—$(CR^3R^4)_p$—D substituents are in the 3 and 5 positions on the Ar phenyl rings; D is Z, wherein Z is the —$C_2HB_{10}H_{10}$ carborane; k, l, u, and w are 0; and e, f, g, and h are 0.

Porphyrin D, a 16-carborane containing porphyrin:

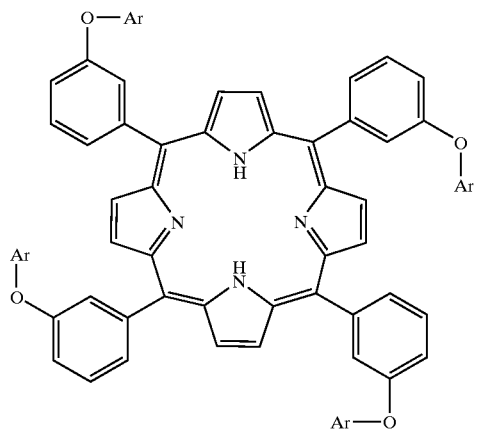

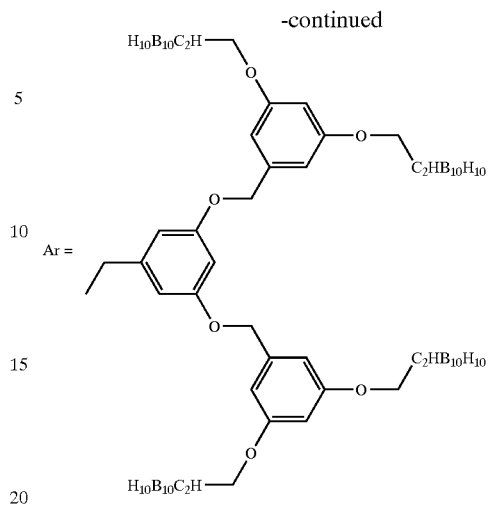

In the case of Porphyrin D above, a, b, c, and d are 1; e, f, g, h, k, l, u, and w are 0; $Y^1$, $Y^2$, $Y^3$, and $Y^4$ are represented by formula (2); $X^1$ and $X^2$ are O; $R^1$, $R^2$, $R^3$ and $R^4$ are H; n and p are 1; m is 2; $Y^1$, $Y^2$, $Y^3$, and $Y^4$ (i.e., O—Ar) are in the meta positions on each phenyl ring; the —$X^2$—$(CR^3R^4)_p$—D substituents are in the 3 and 5 positions on the phenyl ring; D is according to formula (3), wherein $X^3$ is O, $R^{10}$ and $R^{11}$ are H, s is 1, D' is Z, wherein Z is the —$C_qHB_{10}H_{10}$ carborane; q is 2, and i is 0.

The reaction scheme that is currently being employed for the attempted synthesis of the 16-carborane-containing porphyrin above (Porphyrin D), is shown below:

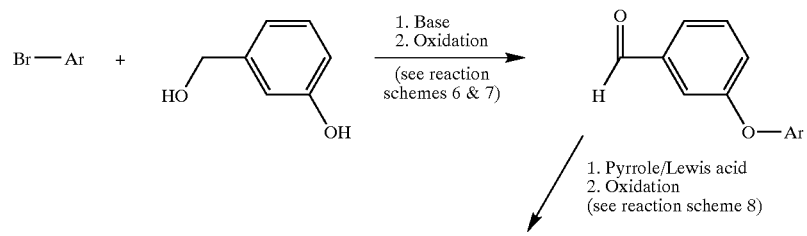

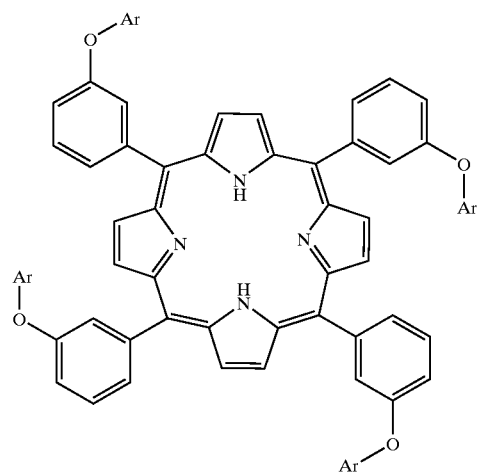

-continued

Ar = 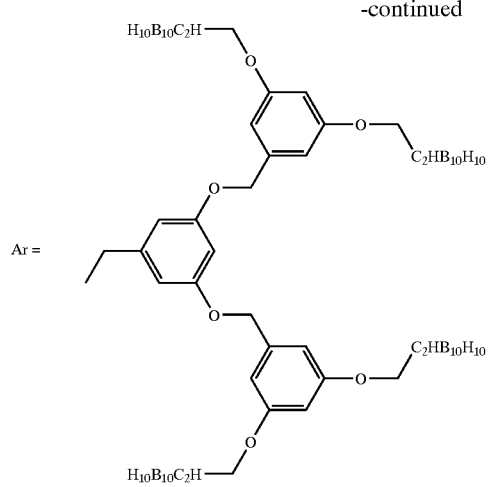

EXAMPLES

Examples have been set forth below for the purpose of illustration and to describe the best mode of the invention at the present time. The scope of the invention is not to be in any way limited by the examples set forth herein.

Example 1

Synthesis of 3,5-dipropargyloxybenzylalcohol (I)

Finely powdered $K_2CO_3$, 14 grams (0.10 moles), and KI, 17 grams (0.10 moles) were placed in a 500 mL round flask, and 200 mL acetone was added. Under a nitrogen atmosphere, 3,5-dihydroxybenzylalcohol, 4.2 grams (0.03 moles), and propargyl chloride, 5.3 grams (0.07 moles) were then added. The resulting mixture was refluxed overnight. The results from thin layer chromatography showed no starting material (3,5-dihydroxybenzylalcohol) as well as the presence of a new compound. The solution was filtered, and the filtered solid washed with acetone. The acetone of the resulting filtrate was removed by rotary evaporation, leaving an organic residue. Dichloromethane (50 mL) was added to dissolve the organic residue, and this was washed with water (30 mL×2), and then dried over anhydrous sodium sulfate. After filtering the organic phase, the solvents were removed by rotary evaporation leaving a yellow oil, which solidified upon standing. 6.3 g of product was obtained, which corresponds to a 97% yield.

The product had a melting point of 79–80° C. and gave the following proton nuclear magnetic resonance ($^1$H NMR) spectrum in ppm (in $CDCl_3$ solvent): 2.52 (triplet, 2H, alkynyl); 2.15 (broad singlet, 1H, hydroxyl); 4.65 (doublet, 4H, $ArOCH_2$); 4.60 (singlet, 2H, $ArCH_2$); 6.52 (singlet, 1H, aryl); 6.60 (singlet, 2H, aryl). The product gave the following proton-decoupled carbon-13 nuclear magnetic resonance ($^{13}$C NMR) spectrum in ppm (in $CDCl_3$ solvent): 56.1 ($ArOCH_2$); 65.1 ($ArCH_2$); 75.9 (alkynyl); 78.6 (alkynyl); 101.6 (aryl); 106.4 (aryl); 143.8 (aryl); 159.0 (aryl). The mass spectrum (FAB) showed a parent ion peak of 217.5 that matched the molecular weight of the compound.

Example 2

Synthesis of 3,5-dipropargyloxybenzylacetate (II)

3,5-dipropargyloxbenzylalcohol (I), 6.3 grams (0.029 moles), was stirred in 7 mL (0.07 moles) acetic anhydride. Two drops of concentrated sulfuric acid was then added to the solution. The solution was stirred in a temperature range of 90–100° C. for three hours. The results from thin layer chromatography showed no starting material (I) as well as the presence of a new compound. The solution was then poured into 50 mL of ice water. Aqueous saturated sodium carbonate solution was added slowly until the pH of the solution was at least 8, at which point there was no further release of carbon dioxide. The aqueous solution was extracted with 50 mL×2 of dichloromethane, and the organic phase was washed with water (50 mL×2) and then dried with anhydrous sodium sulfate. The desired product was purified using a pad of silica in a sintered glass funnel, the pad of silica then washed with 200 mL dichloromethane. The dichloromethane of the filtrate was removed by rotary evaporation, leaving a yellow oil, which solidified upon standing. 7.2 g of product was obtained, which corresponds to a 96% yield.

The product had a melting point of 65–66° C. and gave the following proton nuclear magnetic resonance ($^1$H NMR) spectrum in ppm (in $CDCl_3$ solvent): 2.11 (singlet, 3H, $CH_3$); 2.54 (triplet, 2H, alkynyl); 4.67 (doublet, 4H, $ArOCH_2$); 5.05 (singlet, 2H, $ArCH_2$); 6.58 (singlet, 1H, aryl); 6.61 (singlet, 2H, aryl). The product gave the following proton-decoupled $^{13}$C NMR spectrum in ppm (in $CDCl_3$ solvent): 21.3 ($CH_3$); 56.0 ($ArOCH_2$); 66.2 ($ArCH_2$); 76.2 (alkynyl); 78.6 (alkynyl); 102.3 (aryl); 108.0 (aryl); 138.8 (aryl); 159.0 (aryl); 171.1 (CO). The mass spectrum (FAB) showed a parent ion peak of 259.5 that matched the molecular weight of the compound.

Example 3

Synthesis of 3,5-o-dicarboranylmethoxylbenzylacetate (III)

Decaborane, 2.70 grams, (0.022 moles) was dissolved in 80 mL dry toluene in a 200 mL round-bottomed flask and stirred at room temperature under a nitrogen atmosphere.

Acetonitrile, 12 mL (0.22 moles), was added to the solution by syringe. The solution was then stirred for three hours. A solution composed of 2.84 grams (0.011 moles) 3,5-dipropargyloxybenzylacetate (II) in 80 mL of toluene was then added to the solution by syringe. The resulting mixture was slowly heated to 80–90° C. and stirred in that temperature range for two days. The results from thin layer chromatography showed no starting material (II) as well as the presence of a new compound. The solvents were then removed by rotary evaporation, leaving an organic residue. The organic residue was dissolved in approximately 50 mL of methanol and allowed to stir at reflux for 1 hour to decompose excess decaborane. The methanol was then removed by rotary evaporation. The organic residue was dissolved in 50 mL dichloromethane and then purified using a pad of silica in a sintered glass funnel. The pad of silica was washed with an additional 200 mL of dichloromethane. The dichloromethane of the filtrate was removed by rotary evaporation, leaving a yellow oil, which solidified upon standing. 4.40 grams of product was obtained, which corresponds to an 81% yield.

The product had a melting point of 122–123° C. and gave the following proton nuclear magnetic resonance ($^1$H NMR) spectrum in ppm (in $CDCl_3$ solvent): 2.12 (singlet, 3H, $CH_3$); 4.06 (singlet, 2H, $CCHB_{10}H_{10}$); 4.39 (singlet, 4H, $ArOCH_2$); 5.01 (singlet, 2H, $ArCH_2$); 6.32 (singlet, 1H, aryl); 6.52 (singlet, 2H, aryl). The product gave the following proton-decoupled $^{13}$C NMR spectrum in ppm (in $CDCl_3$ solvent): 21.4 ($CH_3$); 58.3 ($ArOCH_2$); 65.8 ($ArCH_2$); 69.6 ($—CCHB_{10}H_{10}$); 71.5 ($—CCHB_{10}H_{10}$); 102.3 (aryl); 108.5 (aryl); 139.8 (aryl); 158.6 (aryl); 171.0 (CO). The mass spectrum (FAB) showed a parent ion peak of 496.0 that matched the molecular weight of the compound.

Example 4

Synthesis of
3,5-o-dicarboranylmethoxylbenzylalcohol (IV)

Concentrated hydrochloric acid, 4.0 mL, was added to a solution composed of 4.0 grams (8.0 millimoles) 3,5-o-dicarboranyloxymethylbenzylacetate (III) in 60 mL of methanol. The mixture was refluxed for two hours, after which time the results from thin layer chromatography showed no starting material (III) as well as the presence of a new compound. The solvents were then removed by rotary evaporation leaving a yellow oil. On standing at room temperature, the oil solidified to a white solid. 3.4 grams of product was obtained, which corresponds to a 93% yield.

The product had a melting point of 267–269° C. and gave the following proton nuclear magnetic resonance ($^1$H NMR) spectrum in ppm (in $CDCl_3$ solvent): 2.54 (broad singlet, 1H, hydroxyl); 4.04 (singlet, 2H, $CCHB_{10}H_{10}$); 4.40 (singlet, 4H, $ArOCH_2$); 4.65 (singlet, 2H, $ArCH_2$); 6.28 (singlet, 1H, aryl); 6.54 (singlet, 2H, aryl). The product gave the following proton-decoupled $^{13}$C NMR spectrum in ppm (in $CDCl_3$ solvent): 58.0 ($ArOCH_2$); 64.7 ($ArCH_2$); 69.4 ($—CCHB_{10}H_{10}$); 71.3 ($—CCHB_{10}H_{10}$); 101.5 (aryl); 106.6 (aryl); 144.7 (aryl); 158.5 (aryl). The mass spectrum (FAB) showed a parent ion peak of 453.0 that matched the molecular weight of the compound.

Example 5

Synthesis of
3,5-o-dicarboranylmethoxylbenzylbromide (V)

3.5-dicarboranylmethoxylbenzylalcohol (IV), 0.454 grams (1.0 millimoles), and carbon tetrabromide, 0.398 grams (1.2 millimoles), were dissolved in approximately 2 mL of dry tetrahydrofuran. Triphenylphosphine, 0.314 grams (1.2 millimoles), was added to the mixture, and the resulting mixture stirred under an argon atmosphere for 20 minutes. The mixture was then poured into water and the product extracted with dichloromethane (7 mL×3). The dichloromethane extract was dried with anhydrous potassium carbonate and then purified using a silica pad. The silica pad was washed with additional dichloromethane. The dichloromethane filtrate was evaporated to dryness, leaving a white solid. 0.485 grams of product was obtained, which corresponds to a 92% yield.

The product had a melting point of 230–232° C. and gave the following proton nuclear magnetic resonance ($^1$H NMR) spectrum in ppm (in $CDCl_3$ solvent): 4.02 (singlet, 2H, $CCHB_{10}H_{10}$); 4.37 (singlet, 2H, $CH_2Br$); 4.39 (singlet, 4H, $ArOCH_2$); 6.26 (singlet, 1H, aryl); 6.55 (singlet, 2H, aryl). The product gave the following proton-decoupled $^{13}$C NMR spectrum in ppm (in $CDCl_3$ solvent): 32.4 ($CH_2Br$); 58.0 ($ArOCH_2$); 69.5 ($—CCHB_{10}H_{10}$); 71.1 ($—CCHB_{10}H_{10}$); 102.3 (aryl); 109.2 (aryl); 141.2 (aryl); 158.4 (aryl). The mass spectrum (FAB) showed a parent ion peak of 516.9 that matched the molecular weight of the compound.

Example 6

Synthesis of 3-[3,5-o-dicarboranylmethoxybenzyloxy]benzylalcohol (VI)

$K_2CO_3$, 0.210 grams (1.5 millimoles), and KI, 0.25 grams (1.5 millimoles), were placed in a 50 mL round-bottomed flask. 3,5-dicarboranyl-methoxylbenzyl bromide (V), 0.410 grams (0.80 millimoles), 3-hydroxybenzylalcohol, 0.100 grams (0.80 millimoles), and 20 mL acetone, were then added. The mixture was refluxed under an argon atmosphere for 24 hours. The solvent was removed by rotary evaporation, leaving an organic residue. The residue was extracted with 10 mL of dichloromethane, and the organic phase was washed with water in a separatory funnel. The organic phase was then dried over anhydrous potassium carbonate. The dichloromethane was removed by rotary evaporation, leaving a white solid. 0.430 grams of product was obtained, which corresponds to a 96% yield.

The product had a melting point of 259–261° C. and gave the following proton nuclear magnetic resonance ($^1$H NMR) spectrum in ppm (in $CDCl_3$ solvent): 1.70 (singlet, 1H, hydroxyl); 4.04 (singlet, 2H, $CCHB_{10}H_{10}$); 4.40 (singlet, 4H, $CH_2CCHB_{10}H_{10}$); 4.67 (singlet, 2H, $ArCH_2OH$); 5.00 (singlet 2H, $ArCH_2Oar$); 6.31 (singlet, 1H, aryl); 6.60 (singlet, 2H, aryl); 6.87 (multiplet, 1H, aryl); 7.00 (multiplet, 2H, aryl); 7.26 (multiplet, 1H, aryl). The product gave the following proton-decoupled $^{13}$C NMR spectrum in ppm (in $CDCl_3$ solvent): 58.2 ($CH_2CCHB_{10}H_{10}$); 65.5 ($ArCH_2OH$); 69.6 ($—CCHB_{10}H_{10}$); 71.4 ($—CCHB_{10}H_{10}$); 102.0 (aryl); 107.4 (aryl); 113.6 (aryl); 114.3 (aryl); 120.2 (aryl); 130.2 (aryl); 141.2 (aryl); 143.1 (aryl); 158.7 (aryl); 158.8 (aryl). The mass spectrum (FAB) showed a parent ion peak of 559.0 that matched the molecular weight of the compound.

Example 7

Synthesis of 3-[3,5-o-dicarboranylmethoxybenzyloxy]benzaldehyde (VII)

Pyridinum chlorochromate (PCC), 0.172 grams (0.80 millimoles), was dissolved in 10 mL dichloromethane. The resulting solution was cooled in an ice water bath. A solution of 0.223 grams (0.40 millimoles) of 3-[3,5-dicarboranyl-methoxy benzyl]benzyl alcohol (VI) dissolved in 10 mL dichloromethane was added dropwise to the PCC solution. The mixture was stirred for two hours. The results from thin layer chromatography showed no starting material (VI) as well as the presence of a new compound. The major product was purified using a sintered glass funnel containing a 2 centimeter-thick layer of silica. The flask and the layer of silica were washed thoroughly with excess dichloromethane. The solvents were removed by rotary evaporation, leaving a white solid. 0.220 grams of product was obtained, which corresponds to a 99% yields.

The product had a melting point of 263–265° C. and gave the following proton nuclear magnetic resonance ($^1$H NMR) spectrum in ppm (in CDCl$_3$ solvent): 4.04 (singlet, 2H, CCHB$_{10}$H$_{10}$); 4.42 (singlet, 4H, ArOCH$_2$); 5.00 (singlet, 2H, ArCH$_2$O); 6.33 (singlet, 1H, aryl); 6.61 (singlet, 2H, aryl); 7.23 (singlet, 1H, aryl); 7.44 (multiplet, 1H, aryl); 7.50 (multiplet, 2H, aryl); 9.98 (singlet, 1H, CHO). The product gave the following proton-decoupled $^{13}$C NMR spectrum in ppm (in CDCl$_3$ solvent): 58.0 (CH$_2$CCHB$_{10}$H$_{10}$); 69.5 (—CCHB$_{10}$H$_{10}$); 69.7 (ArCH$_2$OAr); 71.2 (—CCHB$_{10}$H$_{10}$); 102.0 (aryl); 107.4 (aryl); 112.8 (aryl); 122.4 (aryl); 124.8 (aryl); 130.6 (aryl); 138.1 (aryl); 138.4 (aryl); 140.3 (aryl); 158.6 (aryl); 192.1 (CHO). The mass spectrum (FAB) showed a parent ion peak of 558.0 that matched the molecular weight of the compound.

Example 8

Synthesis of meso-5,10,15,20-tetrakis[3-(3,5-o-dicarboranylmethoxybenzyloxy)phenyl]porohyrin (VIII)

3-[3,5-o-dicarboranylmethoxybenzyloxy]benzaldehyde (VII), 337 milligrams (0.60 millimoles), 100 mL of dichloromethane, and 420 microliters (0.60 millimoles) of freshly distilled pyrrole, were sequentially transferred to a dry 300 mL round-bottomed flask. The solution was deoxygenated by bubbling argon gas directly into the solution while stirring for 15–20 minutes. BF$_3$ Et$_2$O, 72 microliters of a 1 M dichloromethane solution (0.072 millimoles), was then added. The solution was allowed to stir under an argon atmosphere overnight, after which time the solution became reddish brown. 2,3-dichloro-5,6-dicyano-1.4-benzoquinone (DDQ), 150 milligrams (0.60 millimoles) was then added, which immediately turned the solution very dark. The solution was stirred under reflux for one hour. The major product in the solution was then purified using a 60 mL sintered glass funnel containing about 40 mL of silica. The resulting dark filtrate was rotary evaporated to dryness. The results from thin layer chromatography confirmed the presence of the new purple product as well as some contaminants. The solid was redissolved in dichloromethane and then purified again using another short column of silica eluted with a 1:1 solvent mixture of dichloromethane to hexanes. The results from thin layer chromatography confirmed the absence of the contaminants. The resulting dark filtrate was rotary evaporated to dryness, resulting in a purple product. 78 milligrams of product was obtained, which corresponds to a 22% yield.

The product gave the following proton nuclear magnetic resonance ($^1$H NMR) spectrum in ppm (in CDCl$_3$ solvent): −2.84 (singlet, 2H, NH); 3.97 (singlet, 8H, CCHB$_{10}$H$_{10}$); 4.35 (singlet, 16H, ArOCH$_2$); 5.19 (singlet, 8H, ArCH$_2$); 6.31 (singlet, 4H, aryl); 6.65 (singlet, 8H, aryl); 7.40 (singlet, 4H, aryl); 7.70 (multiplet, 4H, aryl); 7.79 (multiplet, 4H, aryl); 7.86 (multiplet, 4H, aryl); 8.84 singlet, 8H, pyrrole-H). The mass spectrum (FAB) showed a parent ion peak of 2418.3 that matched the molecular weight of the compound. The ultraviolet-visible absorbance spectrum of the product (dichloromethane) showed the following peaks in nanometers of wavelength: 420, 516, 550, 589, and 645.

Example 9

Synthesis of Copper meso-5,10,15,20-tetrakis[3-(3,5-o-dicarboranyl methoxybenzyloxy)phenyl]porphyrin (IX)

A solution of Cu(OAc)$_2$.H$_2$O (6 milligrams, 0.030 millimoles) in 5 mL methanol was added into a solution of porphyrin compound (VIII) (60 milligrams, 0.025 millimoles in 20 mL dichloromethane). The mixture was stirred for 20 minutes. The solvent was then removed by rotary evaporation. The resulting residue was dissolved in dichloromethane, washed with water and then dried over anhydrous sodium sulfate. The drying agent was filtered off. The solvent of the filtrate was removed by rotary evaporation, leaving a red solid residue. The solid was re-dissolved in dichloromethane and purified using a silica pad eluting with a 1:1 solvent mixture of hexane and dichloromethane. The solvents were removed by rotary evaporation, leaving the red copper porphyrin compound, 57 milligrams of product, which corresponds to a 92% yield.

The mass spectrum (FAB) showed a parent ion peak of 2479.9 that matched the molecular weight of the compound. The ultraviolet-visible absorbance spectrum of the product showed the following peaks in nanometers of wavelength (in dichloromethane solvent): 416, 539.

Example 10

Preparation of Boronated Porphyrin Solutions

Porphyrin compound (IX) was emulsified in 9% Cremophor EL and 18% propylene glycol in saline to give a porphyrin concentration of approximately 2.9 mg/mL. To prepare a solution of ~2.9 mg/mL porphyrin in 9% Cremophor EL (CRM) and 18% propylene glycol (PRG), the porphyrin was dissolved in tetrahydrofuran (THF) (1.5% of the total volume) and then heated to 40° C. for 15 min. CRM (9% of total volume) was then added and the mixture was heated to 60° C. for 2 hours, which removed most of the THF. After cooling to room temperature, PRG (18% of total volume) was added, followed by slow dropwise addition of saline (71.5% of total volume) with rapid stirring. The solution was degassed by stirring under vacuum (~30 mm Hg) for 30–60 min and then filtered (Millipore, 8 µm).

Example 11

Biodistribution of Porphyrin IX in Mice Bearing EMT-6 Carcinomas

BALB/c mice bearing subcutaneously implanted EMT-6 mammary carcinomas implanted on the dorsal thorax were given a total dose of 87 milligrams porphyrin compound (IX) per kilogram body weight (30 mg B/kg) in 3 intraperitoneal (i.p.) injections over a period of 8 hours. At two and four days after the last injection, mice were euthanized, and tumor, blood, brain, and liver were removed for boron analyses. The blood was first analyzed for hematologic parameters that indicate toxicity before it was analyzed for boron. Table 1 below shows the average boron concentrations for different types of tissue in five of the BALB/c mice in milligram of porphyrin compound (IX) per kilogram body weight.

TABLE 1

Average boron concentrations (µg/g) in various tissues in mice (n = 5) given 87 mg/kg porphyrin (IX) (30 mg B/kg) in 3 i.p. injections over a period of 8 hours.

| Time after last injection | EMT-6 Tumor µg B/g | Blood µg B/g | Brain µg B/g | Liver µg B/g |
|---|---|---|---|---|
| 2 days | 43.5 ± 10.0 | 0.5 ± 0.2 | 0.2 ± 0.0 | 353 ± 55 |
| 4 days | 27.8 ± 7.6 | 0.2 ± 0.1 | 0.3 ± 0.2 | 250 ± 70 |

Example 12

Weight Changes and Hematologic Parameters from Porphyrin (IX)

TABLE 2

Weight changes and hematologic parameters in mice given 87 mg/kg porphyrin (IX) (30 mg B/kg) or solvent only (9% Cremophor and 18% propylene glycol in saline) at 2 or 4 days after the last injection. Values are reported as median (and range).

| Compound | Time after last injection | Number of mice | % Weight change | Platelets ($10^3/mm^3$) | Lymphocytes (% WBC) | Granulocytes (% WBC) |
|---|---|---|---|---|---|---|
| Porphyrin compound (IX) | 2 days | 5 | 0.4 (−4.9–2.5) | 193 (51–432) | 44 (37–56) | 53 (42–60) |
| Solvent only | 2 days | 4 | −1.3 (−4.5–1.1) | 640 (568–730) | 68 (61–71) | 28 (26–32) |
| Porphyrin compound (IX) | 4 days | 5 | −0.6 (−4.7–1.5) | 917 (670–1128) | 35 (30–39) | 62 (57–67) |
| Solvent only | 4 days | 4 | −0.7 (2.2–2.1) | 527 (500–618) | 71 (70–72) | 26 (24–26) |

The results of the preliminary biodistribution study showed that the tumor boron concentrations are adequate for therapy, particularly at the two-day time-point. The tumor to blood boron ratios are quite high, which are more than 80:1, and tumor to brain ratios are even higher. The platelet data indicate a small but significant decrease in the porphyrin-administered mice at the 2-day time point compared to the solvent-only mice. However, by the 4-day time point, the platelet counts have rebounded to a level greater than those from the solvent-only group. The weight data indicate that the level of toxicity is very low if it exists at all since there were no differences between porphyrin- and solvent-injected mice. Thus, it is possible that the doses can be escalated significantly without affecting toxicity.

Thus, while there have been described the preferred embodiments of the present invention, those skilled in the art will realize that other embodiments can be made without departing from the spirit of the invention, which includes all such further modifications and changes as come within the true scope of the claims set forth herein.

What is claimed is:

1. A compound of the formula

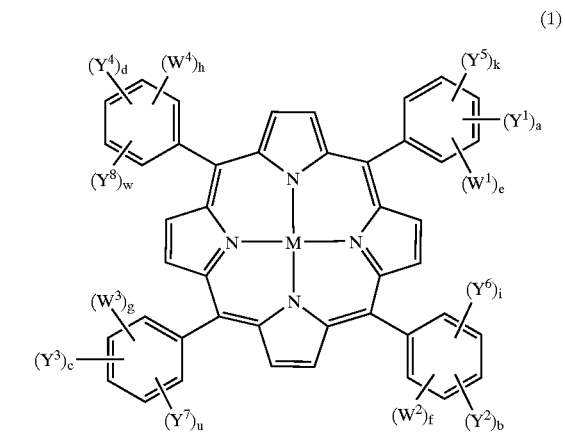

(1)

wherein:

$Y^1$, $Y^2$, $Y^3$, and $Y^4$ are independently on the ortho, meta or para position on the phenyl rings, and are independently hydrogen, alkyl, cycloalkyl, aryl, alkylaryl, arylalkyl, heteroaryl, or an alkyl, cycloalkyl, aryl, alkylaryl, arylalkyl, or heteroaryl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide; or a substituent represented by the formula

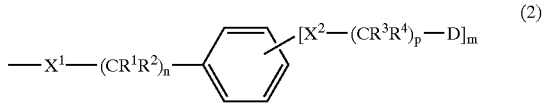

(2)

wherein D represents independently, Z, hydrogen, or a substituent represented by the formula

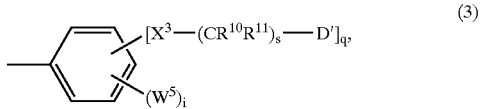

provided that at least one D is Z or is represented by formula (3);

wherein D' represents independently, Z, hydrogen, or a substituent represented by the formula

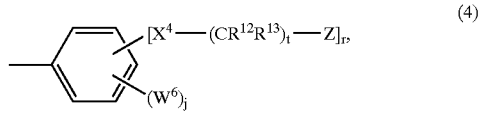

provided that when q is 0, or when q is not zero and D' is solely hydrogen, then at least one D is represented by Z, or when q is not zero and D' is represented by formula (4) and r is zero, then at least one D is represented by Z;

$Y^5$, $Y^6$, $Y^7$, and $Y^8$ are independently on the ortho, meta or para position on the phenyl rings, and are represented by the formula $$—X^a—(CR^aR^b)_v—Z \qquad (5);$$

$W^1$, $W^2$, $W^3$, $W^4$, $W^5$, and $W^6$ are hydrophilic groups independently on the ortho, meta or para position on the phenyl rings, and are independently selected from hydroxy, alkoxy, — $C(O)OR^5$, —$SOR^6$, —$SO_2R^6$, nitro, amido, ureido, carbamato, —$SR^7$, —$NR^8R^9$, or polyalkylene oxide;

$X^a$, $X^1$, $X^2$, $X^3$, and $X^4$ are independently oxygen or sulfur;

$R^a$, $R^b$, $R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from hydrogen and $C_1$ to $C_4$ alkyl;

Z is a carborane cluster comprising at least two carbon atoms and at least three boron atoms, or at least one carbon atom and at least five boron atoms, within a cage structure;

n, p, s, t, and v independently represent 0, or an integer from 1 to 20;

m independently represents 1, 2, or 3;

q and r independently represent 0, 1, 2, or 3;

a, b, c, and d independently represent 1 or 2;

k, l, u, and w independently represent 0, 1, or 2;

e, f, g, h, i, and j independently represent 0, or an integer from 1 to 5;

provided that at least one of $Y^1$, $Y^2$, $Y^3$, and $Y^4$ represents formula (2); each of the sums a+e+k, b+f+l, c+g+u, h+d+w, q+i, r+j, independently represents an integer from 1 to 5; when any of k, l, u, or w is not zero, then at least one of $Y^1$, $Y^2$, $Y^3$, and $Y^4$ represents formula (2); and M is either two hydrogen ions; a single monovalent metal ion; two monovalent metal ions; a divalent metal ion; a trivalent metal ion; a tetravalent metal ion; a pentavalent metal ion; a hexavalent metal ion; a radioactive metal ion useful in radioisotope-mediated radiation therapy or imageable by single photon emission computed tomography (SPECT) or positron emission tomography (PET); a paramagnetic metal ion detectable by magnetic resonance imaging (MRI); a metal ion suitable for boron neutron capture therapy (BNCT) or photodynamic therapy (PDT); or a combination thereof; wherein the porphyrin-metal complex derived from a single monovalent metal ion is charge-balanced by a counter cation, and the porphyrin-metal complex derived from a trivalent, tetravalent, pentavalent, hexavalent metal ion is charge-balanced by an appropriate number of counter anions, dianions, or trianions.

2. The compound according to claim 1 wherein Z is selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

3. The compound according to claim 1, wherein M is vanadium, manganese, iron, ruthenium, technetium, chromium, platinum, cobalt, nickel, copper, zinc, germanium, indium, tin, yttrium, gold, barium, tungsten, or gadolinium.

4. The compound according to claim 1 wherein a, b, c, and d are 1, and $Y^1$, $Y^2$, $Y^3$, and $Y^4$ are represented by

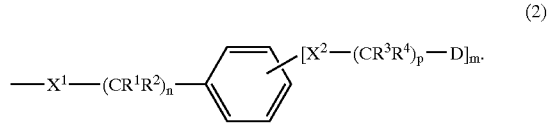

5. The compound according to claim 4 wherein D is Z, wherein Z is selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

6. The compound according to claim 5, wherein M is vanadium, manganese, iron, ruthenium, technetium, chromium, platinum, cobalt, nickel, copper, zinc, germanium, indium, tin, yttrium, gold, barium, tungsten, or gadolinium.

7. The compound according to claim 6, wherein $X^1$ and $X^2$ are O; $R^1$, $R^2$, $R^3$ and $R^4$ are H; n and p are 1; and m is 2.

8. The compound according to claim 7 wherein $Y^1$, $Y^2$, $Y^3$, and $Y^4$ are in a meta position on each phenyl ring.

9. The compound according to claim 8 wherein the —$X^2$—$(CR^3R^4)_p$—D substituents are in the 3 and 5 positions on each phenyl ring.

10. The compound according to claim 8 wherein the —$X^2$—$(CR^3R^4)_p$—D substituents are in the 3 and 4 positions on the phenyl ring.

11. The compound according to claim 9 wherein e, f, g, h, k, l, u, and w are 0.

12. The compound according to claim 7, wherein e, f, g, and h are 1 and k, l, u, and w are 0.

13. The compound according to claim 12, wherein $W^1$, $W^2$, $W^3$, and $W^4$ are independently, hydroxy or alkoxy.

14. The compound according to claim 13, wherein $W^1$, $W^2$, $W^3$, and $W^4$ are alkoxy.

15. The compound according to claim 14, wherein alkoxy is methoxy.

16. The compound according to claim 15, wherein $Y^1$, $Y^2$, $Y^3$, and $Y^4$ are in the para position on each phenyl ring.

17. The compound according to claim 16, wherein $W^1$, $W^2$, $W^3$, and $W^4$ are in a meta position of each phenyl ring.

18. The compound according to claim 17 wherein the —$X^2$—$(CR^3R^4)_p$—D substituents are in the 3 and 5 positions of each phenyl ring.

19. The compound according to claim 17 wherein the —$X^2$—$(CR^3R^4)_p$—D substituents are in the 3 and 4 positions of the phenyl ring.

20. The compound according to claim 9 wherein k, l, u, and w are 1.

21. The compound according to claim 20, wherein $Y^5$, $Y^6$, $Y^7$, and $Y^8$ are in the para position on each phenyl ring.

22. The compound according to claim 21 wherein the —$X^a$—$(CR^aR^b)_v$—Z substituents are in the 3 and 5 positions on each phenyl ring.

23. The compound according to claim 21 wherein the —$X^a$—$(CR^aR^b)_v$—Z substituents are in the 3 and 4 positions on the phenyl ring.

24. The compound according to claim 22 or 23 wherein $X^a$ is O; $R^a$ and $R^b$ are H; v is 1, and Z is selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

25. The compound according to claim 24, wherein e, f, g, and h are 0.

26. The compound according to claim 1 wherein a, b, c, and d are 2, and $Y^1$, $Y^2$, $Y^3$, and $Y^4$ are represented by

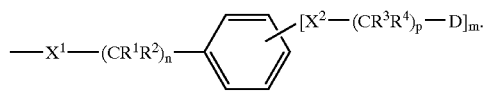

(2)

27. The compound according to claim 26 wherein D is Z, and Z is selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

28. The compound according to claim 27, wherein M is vanadium, manganese, iron, ruthenium, technetium, chromium, platinum, cobalt, nickel, copper, zinc, germanium, indium, tin, yttrium, gold, barium, tungsten, or gadolinium.

29. The compound according to claim 28, wherein $X^1$ and $X^2$ are O; $R^1$, $R^2$, $R^3$ and $R^4$ are H; n and p are 1; and m is 2.

30. The compound according to claim 29, wherein $Y^1$, $Y^2$, $Y^3$, and $Y^4$ are in the two meta positions on each phenyl ring.

31. The compound according to claim 30, wherein the —$X^2$—$(CR^3R^4)_p$—D substituents are in the 3 and 5 positions on each phenyl ring.

32. The compound according to claim 30, wherein the —$X^2$—$(CR^3R^4)_p$—D substituents are in the 3 and 4 positions on the phenyl ring.

33. The compound according to claim 31 or 32, wherein k, l, u, and w are 0.

34. The compound according to claim 33, wherein e, f, g, and h are 0.

35. The compound according to claim 4, wherein $X^1$ and $X^2$ are O; $R^1$, $R^2$, $R^3$ and $R^4$ are H; n and p are 1; m is 2, and D is represented by

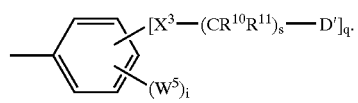

(3)

36. The compound according to claim 35, wherein $X^3$ is O, $R^{10}$ and $R^{11}$ are H, s is 1, D' is Z, q is 2, and i is 0, wherein Z is selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

37. A method of imaging a tumor and surrounding tissue in a subject comprising the administration to the subject of a composition comprising a compound according to claim 1; and the imaging of said subject.

38. A method of imaging a tumor and surrounding tissue in a subject comprising the administration to the subject of a composition comprising a compound according to claim 11; and the imaging of said subject.

39. A method of imaging a tumor and surrounding tissue in a subject comprising the administration to the subject of a composition comprising a compound according to claim 18; and the imaging of said subject.

40. A method of imaging a tumor and surrounding tissue in a subject comprising the administration to the subject of a composition comprising a compound according to claim 25; and the imaging of said subject.

41. A method of imaging a tumor and surrounding tissue in a subject comprising the administration to the subject of a composition comprising a compound according to claim 34; and the imaging of said subject.

42. A method of imaging a tumor and surrounding tissue in a subject comprising the administration to the subject of a composition comprising a compound according to claim 36; and the imaging of said subject.

43. The method according to any of claims 37, 38, 39, 40, 41, or 42 wherein said imaging is by a method selected from magnetic resonance imaging (MRI), single photon emission computed tomography (SPECT), or positron emission tomography (PET) methods.

44. A method of bimodal cancer treatment in a subject comprising the administration to the subject of a composition comprising a compound according to claim 1; and the irradiation of said subject.

45. A method of bimodal cancer treatment in a subject comprising the administration to the subject of a composition comprising a compound according to claim 11; and the irradiation of said subject.

46. A method of bimodal cancer treatment in a subject comprising the administration to the subject of a composition comprising a compound according to claim 18; and the irradiation of said subject.

47. A method of bimodal cancer treatment in a subject comprising the administration to the subject of a composition comprising a compound according to claim 25; and the irradiation of said subject.

48. A method of bimodal cancer treatment in a subject comprising the administration to the subject of a composition comprising a compound according to claim 34; and the irradiation of said subject.

49. A method of bimodal cancer treatment in a subject comprising the administration to the subject of a composition comprising a compound according to claim 36; and the irradiation of said subject.

50. The method according to any of claims 44, 45, 46, 47, 48, or 49 wherein said irradiation is by a method utilizing thermal or epithermal neutrons, or laser red light.

51. The method according to claim 44, wherein said bimodal cancer treatment comprises boron neutron capture therapy (BNCT).

52. The method according to claim 44, wherein said bimodal cancer treatment comprises photodynamic therapy (PDT).

53. The method according to claim 44, wherein said bimodal cancer treatment utilizes single photon emission computed tomography (SPECT) or positron emission tomography (PET) wherein M is a SPECT- and/or PET-imageable radioactive metal ion.

54. The method according to claim 44, wherein said bimodal cancer treatment utilizes magnetic resonance imaging (MRI) wherein M is a paramagnetic metal ion.

55. The compound according to claim 1 wherein the counter dianion is a porphyrin compound containing a divalent negative charge.

56. The compound according to claim 55, wherein the porphyrin compound containing a divalent negative charge is the compound of claim 1, with the proviso that M is absent.

* * * * *